US008058056B2

(12) United States Patent
Lee et al.

(10) Patent No.: US 8,058,056 B2
(45) Date of Patent: Nov. 15, 2011

(54) METHOD AND APPARATUS FOR INTEGRATED CELL HANDLING AND MEASUREMENTS

(75) Inventors: Luke P. Lee, Orinda, CA (US); Jeonggi Seo, Albany, CA (US); Cristian Ionescu-Zanetti, Berkeley, CA (US); Michelle Khine, Merced, CA (US); Adrian Lau, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 779 days.

(21) Appl. No.: 11/466,104

(22) Filed: Aug. 21, 2006
(Under 37 CFR 1.47)

(65) Prior Publication Data
US 2007/0155016 A1    Jul. 5, 2007

Related U.S. Application Data

(63) Continuation-in-part of application No. PCT/US2005/008349, filed on Mar. 14, 2005.

(60) Provisional application No. 60/710,305, filed on Aug. 21, 2005, provisional application No. 60/552,892, filed on Mar. 12, 2004.

(51) Int. Cl.
C12M 3/00    (2006.01)
(52) U.S. Cl. ............. 435/288.5; 435/287.1; 204/403.01; 204/403.03; 204/403.13; 422/82.01
(58) Field of Classification Search ................ 435/287.1, 435/288.5; 204/403.01, 403.03, 403.13; 422/82.01
See application file for complete search history.

(56) References Cited

U.S. PATENT DOCUMENTS

| | | |
|---|---|---|
| 5,744,366 A | 4/1998 | Kricka |
| 5,842,787 A | 12/1998 | Kopf-sill et al. |
| 5,885,470 A * | 3/1999 | Parce et al. ............. 216/33 |
| 5,942,443 A | 8/1999 | Parce et al. |
| 6,068,752 A | 5/2000 | Dubrow et al. |
| 6,153,073 A | 11/2000 | Dubrow et al. |
| 6,238,538 B1 | 5/2001 | Parce et al. |
| 6,251,343 B1 | 6/2001 | Dubrow et al. |
| 6,274,337 B1 | 8/2001 | Parce et al. |
| 6,315,940 B1 | 11/2001 | Nisch et al. |
| 6,403,348 B1 * | 6/2002 | Rubinsky et al. ......... 435/173.7 |
| 6,413,782 B1 | 7/2002 | Parce et al. |
| 6,429,025 B1 | 8/2002 | Parce et al. |
| 6,432,630 B1 | 8/2002 | Blankenstein |
| 6,437,551 B1 | 8/2002 | Krulevitch et al. |
| 6,454,945 B1 | 9/2002 | Weigl et al. |
| 6,479,299 B1 | 11/2002 | Parce et al. |
| 6,540,895 B1 | 4/2003 | Spence et al. |
| 6,562,604 B2 | 5/2003 | Rubinsky et al. |
| 6,589,729 B2 | 7/2003 | Chan et al. |
| 6,592,821 B1 | 7/2003 | Wada et al. |
| 6,632,619 B1 | 10/2003 | Harrison et al. |
| 6,653,089 B2 | 11/2003 | Takayama et al. |
| 6,686,184 B1 | 2/2004 | Anderson et al. |
| 6,686,193 B2 | 2/2004 | Maher et al. |
| 6,699,697 B2 | 3/2004 | Klemic et al. |
| 6,742,661 B1 | 6/2004 | Schulte et al. |
| 6,759,191 B2 | 7/2004 | Farinas et al. |
| 6,770,434 B2 | 8/2004 | Shvets et al. |
| 6,776,896 B1 | 8/2004 | Osipchuk |
| 6,899,800 B2 | 5/2005 | Osipchuk et al. |
| 6,900,021 B1 | 5/2005 | Harrison et al. |
| 6,927,049 B2 | 8/2005 | Rubinsky et al. |
| 6,932,893 B2 | 8/2005 | Bech et al. |
| 6,936,462 B1 | 8/2005 | Owen et al. |
| 6,969,604 B1 | 11/2005 | Yakovenko |
| 6,979,553 B2 | 12/2005 | Farinas et al. |
| 6,989,089 B2 | 1/2006 | Nisch et al. |
| 7,013,739 B2 | 3/2006 | Schroeder et al. |
| 7,018,819 B2 | 3/2006 | Orwar et al. |
| 7,067,263 B2 | 6/2006 | Parce et al. |
| 7,112,433 B2 | 9/2006 | Tyvoll et al. |
| 7,122,301 B2 | 10/2006 | Shvets et al. |
| 7,176,016 B2 | 2/2007 | Maher et al. |
| 7,214,298 B2 | 5/2007 | Spence et al. |
| 7,221,455 B2 | 5/2007 | Chediak et al. |
| 7,241,565 B2 | 7/2007 | Bullen et al. |
| 7,244,349 B2 | 7/2007 | Vogel et al. |
| 7,288,785 B2 | 10/2007 | Vestergaard et al. |
| 7,312,085 B2 | 12/2007 | Chou et al. |
| 7,358,077 B2 | 4/2008 | Zimmermann et al. |

(Continued)

FOREIGN PATENT DOCUMENTS
EP         0708331         4/1996
(Continued)

OTHER PUBLICATIONS

Matthews and Judy, "Characterization of a micromachined planar patch clamp for cellular electrophysiology", 1st International IEEE EMBS Neural Engineering Conference, 2003, Capri, Italy (Mar. 20-22). Orwar et al., "System and method for for obtaining and maintaining high-resistance seals in patch clamp recording," U.S. Appl. No. 60/404,886, filed Aug. 21, 2002.
Extended supplementary European search report dated Mar. 24, 2010 for European Patent Application No. 07759449.7.
Office action mailed Jun. 21, 2010 in connection with U.S. Appl. No. 11/690,831.
International search report dated Dec. 2, 2005 for PCT Application No. US2005/08349.
International search report dated Dec. 7, 2007 for PCT Application No. US2007/65001.
Thorsen, et al. Microfluidic large-scale integration. Science. Oct. 18, 2002;298(5593):580-4.
Amaxa Biosystems. Available at: http://www.amaxa.com/96-wellnucleofection.html. Accessed Jan. 8, 2008.
Ambion. The RNA Company, siPorter TM 96 Electroporation Chamber. Available at http://www.ambion.com/catalog/CatNum.php?13500. Accessed Jan. 8, 2008.

(Continued)

Primary Examiner — Allison M. Ford
Assistant Examiner — Susan E Fernandez
(74) Attorney, Agent, or Firm — Quine Intellectual Property Law Group, P.C.; Stephen J. LeBlanc

(57) ABSTRACT

Method and systems provide improved cell handling in microfluidic systems and devices using lateral cell trapping and methods of fabrication of the same that allow for selective low voltage electroporation and electrofusion.

33 Claims, 21 Drawing Sheets

U.S. PATENT DOCUMENTS

| | | | |
|---|---|---|---|
| 7,361,500 B2 | 4/2008 | Stett et al. |
| 7,390,650 B2 | 6/2008 | Karlsson et al. |
| 7,452,726 B2 | 11/2008 | Chou et al. |
| 7,470,518 B2 | 12/2008 | Chiu et al. |
| 7,563,614 B2 | 7/2009 | Orwar et al. |
| 2002/0039783 A1 | 4/2002 | McMillan |
| 2002/0045566 A1 | 4/2002 | Gribkoff et al. |
| 2002/0064841 A1 | 5/2002 | Klemic et al. |
| 2002/0164777 A1 | 11/2002 | Kelly et al. |
| 2002/0182627 A1 | 12/2002 | Wang et al. |
| 2002/0182642 A1 | 12/2002 | Orwar et al. |
| 2002/0195337 A1 | 12/2002 | Osipchuk et al. |
| 2003/0022268 A1 | 1/2003 | Lepple-Wienhues |
| 2003/0065452 A1 | 4/2003 | Hickman |
| 2003/0121778 A1 | 7/2003 | Dodgson et al. |
| 2003/0129581 A1 | 7/2003 | Owen et al. |
| 2003/0138767 A1 | 7/2003 | Bullen et al. |
| 2003/0139336 A1 | 7/2003 | Norwood et al. |
| 2003/0143720 A1 | 7/2003 | Hickman |
| 2003/0153067 A1 | 8/2003 | Stett et al. |
| 2003/0153076 A1 | 8/2003 | Villeponteau et al. |
| 2003/0159999 A1 | 8/2003 | Oakey |
| 2003/0180965 A1 | 9/2003 | Yobas et al. |
| 2003/0199050 A1 | 10/2003 | Mangano et al. |
| 2003/0219884 A1 | 11/2003 | Lison et al. |
| 2003/0224531 A1 | 12/2003 | Brennen et al. |
| 2004/0005696 A1 | 1/2004 | Vesterguard et al. |
| 2004/0005901 A1 | 1/2004 | Ala-Luukko |
| 2004/0106126 A1 | 6/2004 | Fendler |
| 2004/0146849 A1 | 7/2004 | Huang et al. |
| 2004/0229349 A1 | 11/2004 | Daridon |
| 2005/0009004 A1 | 1/2005 | Xu et al. |
| 2005/0026283 A1 | 2/2005 | Ormar et al. |
| 2005/0058990 A1 | 3/2005 | Guia et al. |
| 2005/0070018 A1 | 3/2005 | Johnson et al. |
| 2005/0118723 A1 | 6/2005 | Padmanabhan |
| 2005/0129581 A1 | 6/2005 | McBride et al. |
| 2005/0170510 A1 | 8/2005 | Huang et al. |
| 2005/0196746 A1 | 9/2005 | Xu et al. |
| 2005/0224351 A1 | 10/2005 | Ungar et al. |
| 2005/0266478 A1 | 12/2005 | Huang et al. |
| 2006/0003310 A1 | 1/2006 | Klauke et al. |
| 2006/0006067 A1 | 1/2006 | Unger |
| 2006/0194255 A1 | 8/2006 | Finkel |
| 2006/0234298 A1 | 10/2006 | Chiu et al. |
| 2007/0155016 A1 | 7/2007 | Lee et al. |
| 2007/0243523 A1 | 10/2007 | Ionescu-Zanetti et al. |
| 2009/0209029 A1 | 8/2009 | Guia et al. |

FOREIGN PATENT DOCUMENTS

| | | | |
|---|---|---|---|
| EP | 0708331 A1 | 4/1996 |
| EP | 1448771 B1 | 8/2004 |
| EP | 1597576 B1 | 11/2005 |
| GB | 2 371 626 A | 7/2002 |
| WO | WO9852691 A1 | 11/1998 |
| WO | WO9955827 A1 | 11/1999 |
| WO | WO2005089253 A2 | 9/2005 |
| WO | WO2007008609 A2 | 1/2007 |
| WO | WO2005089253 A3 | 3/2007 |
| WO | WO2007024701 A2 | 3/2007 |
| WO | WO 2008/072029 | 6/2008 |

OTHER PUBLICATIONS

Axoporator 800A. Molecular Devices. Available at: http://moleculardevices.com/pages/instruments/cn_axoporator800.html. Accessed on Aug. 13, 2008.

BIO-RAD.COM. Available at: http://www.bio-rad.com/B2B/BioRad/product/br_category.jsp?BV_SessionID=@@@@1456209995.1143592729@@@@&BV_EngineID=cccdaddhgikgikhcfngcfkmdhkkdfll.0&loggedIn=false&lang=English&divName=Corporate&country=HQ&categoryPath=/Catalogs/.

BTX Molecular Delivery Systems. Available at: http://www.btxonline.com/products/advancedtransfection/default.asp. Accessed Jan. 7, 2008.

Amendment in Response to Non-Final Office Action mailed Jun. 25, 2009 for U.S. Appl. No. 11/466,104.

Non-Final Office Action mailed Feb. 25, 2010 for U.S. Appl. No. 11/690,831.

Non-Final Office Action mailed Jul. 23, 2010 for U.S. Appl. No. 11/466,104.

Non-Final Office Action mailed Jun. 21, 2010 for U.S. Appl. No. 11/690,831.

Non-Final office action mailed Jun. 25, 2009 in U.S. Appl. No. 11/466,104.

Non-Final Requirement for Restriction/Election mailed Nov. 17, 2008 for U.S. Appl. No. 11/466,104.

Response to Non-Final Requirement for Restriction/Election mailed Nov. 17, 2008 for U.S. Appl. No. 11/466,104.

Response to Non-Final Office Action mailed Jun. 21, 2010 for U.S. Appl. No. 11/690,831.

Response to Non-Final Restriction Requirement for U.S. Appl. No. 11/690,831.

U.S. Appl. No. 60/710,305, entitled "Cell Handling, Electroporation and Electrofusion in Microfluidic System", filed Aug. 21, 2005.

European Search Report dated Apr. 16, 2010 for Application No. PCT/US2007065001.

Ausubel, et al., (Eds.) Current Protocols in Molecular Biology. vols. I, II and III 1997, Table of Contents.

Ausubel, et al., (Eds.), Short Protocols in Molecular Biology: A Compendium of Methods from Current Protocols in Molecular Biology. 5th Ed. John Wiley & Sons, Inc. 2002, Table of Contents.

Batzer, et al., "Enhanced evolutionary PCR using oligonucleotides with inosine at the 3'-terminus", Nucleic Acids Res 1991, 19(18): 5081.

Bennett, et al., "Trends in ion channel drug discovery: advances in screening technologies", Trends Biotechnol. 2003, 21(12): 563-569.

Bonetta, et al., "Flow cytometry smaller and better", Nature Methods 2005, 2(10): 785-795.

Brown, et al., "Improvements to parallel plate flow chambers to reduce reagent and cellular requirements", BMC Immunol. 2001, 2:9.

Burnett, et al., "Fluorescence imaging of electrically stimulated cells", J Biomol Screen Dec. 2003, 8:660-667.

Denyer, et al., "HTS approaches to voltage-gated ion channel drug discovery", Drug Discovery Today 1998, 3(7): 323-332.

Innis, et al., (Eds.) PCR Protocols: A Guide to Methods and Applications. Elsevier Science & Technology Books 1990, Table of Contents.

Ionescu-Zanetti, et al., U.S. Appl. No. 60/744,034, entitled "Methods and Apparatus for Intercellular Delivery and Electrophysiology" filed Mar. 31, 2006 (WSGR Reference No. 32321-701.101).

Ionescu-Zanetti, et al., U.S. Appl. No. 60/868,864, entitled "Methods and Apparatus for a Stop-Flow Imaging Cytometer", filed Dec. 6, 2006 (WSGR Reference No. 32321-703.101).

Ionescu-Zanettti, et al., "Mammalian Electrophysiology on a Microfluidic Platform", PNAS 2005, 102(20): 9112-9117.

Khine, et al., "A Single Cell Electroporation Chip", Lab Chip 2005, 5: 38-43.

Li, et al., "Transport, Manipulation, and Reaction of Biological Cells on-chip using electrokinetic effects", Anal Chem. 1997, 69: 1564-1568.

Lu, et al., "Microfluidic shear devices for quantitative analysis of cell adhesion", Anal Chem. 2004, 76: 5257-5264.

Orwar, et al., "System and method for obtaining and maintaining high-resistance seals in patch clamp recording", U.S. Appl. No. 60/404,886, filed Aug. 21, 2002.

Schroeder, et al., "InoWorks (TM) HT: A new high-throughput electrophysiology measurement platform", Journal of Biomolecular Screening 2003, 8(1): 50-64.

Southan, et al., "Ion Channels—New Opportunities for an Established Target Class", Drug Discovery World 2005, 6(3): 17-23.

Steel, et al., "The Flow Thru Chip: A 3-D Biochip platform microarray Biochip Technology", Eaton Publishing, Mass. 2000, pp. 87-117.

Abidor, et al. 246-Electric breakdown of bilayer lipid membranes. I. The main experimental facts and their qualitative discussion. Bioelectrochem. Bioenerg. 1979; 6:37-52.

Akinlaja, et al. The Breakdown of Cell Membranes by Electrical and Mechanical Stress. Biophys J., 1998, 75, 247-254.

Asmild, et al., Upscaling and Automation of Electrophysiology: Toward High Throughput Screening in Ion Channel Drug Discovery. Receptors and Channels, 2003; 9:49-58.

Burnett, et al. Fluorescence imaging of electrically stimulated cells. J Biomol Screen. Dec. 2003;8(6):660-7.

Chang, et al. Guide to Electroporation and Electrofusion. Academic Press 1992, Table of Contents.

Dove, A. Screening for content—the evolution of high throughput. Nature Biotechnology. 2003; 21:859-864.

Entzeroth, M. Emerging trends in high-throughput screening. Current Opinion in Pharmacology. 2003; 3:522-529.

Fertig, et al. Activity of single ion channel proteins detected with a planar microstructure. Applied Physics Letters. 2002; 81:4865-4867.

Fertig, et al. Stable integration of isolated cell membrane patches in a nanomachined aperture. Appl. Phys. Lett. 2000; 77:1218-1220.

Fertig, et al., Whole Cell Patch Clamp Recording Performed on a Planar Glass Chip. Biophysical Journal 2002, 82:3056-3062.

Gill, et al. Flux assays in high throughput screening of ion channels in drug discovery. Assay Drug Dev Technol. Oct. 2003;1(5):709-17.

Huang, et al. Microfabricated electroporation chip for single cell membrane permeabilization. Sens. Actuators, A. 2001; 89:242-249.

Immke, et al. Ion-Ion interactions at the selectivity filter. Evidence from K(+)—dependent modulation of tetraethylammonium efficacy in Kv2.1 potassium channels. J Gen Physiol. Apr. 2000;115(4):509-18.

Lehnert, et al., Realization of hollow SIO2 micronozzles for electrical measurements on living cells. Applied Physics Letters 2002, 81:5063-5065.

Lin, et al. Structure formation at the interface of liquid/liquid bilayer in electric field. Macromolecules. 2002; 35:3971-3976.

Lundqvist, et al. Altering the biochemical state of individual cultured cells and organelles with ultramicroelectrodes. Proc Natl Acad Sci U S A. Sep. 1, 1998;95(18):10356-60.

Needham, et al. Electro-mechanical permeabilization of lipid vesicles. Role of membrane tension and compressibility. Biophys J. May 1989;55(5):1001-9.

Neubert, H. J. Patch clamping moves to chips. Anal Chem. Sep. 1, 2004;76(17):327A-330A.

Neumann, et al. Gene transfer into mouse lyoma cells by electroporation in high electric fields. EMBO J. 1982;1(7):841-5.

Neumann, et al. Mechanism of electroporative dye uptake by mouse B cells. Biophys J. Jan. 1998;74(1):98-108.

Nolkrantz, et al. Electroporation of Single Cells and Tissues with an Electrolyte-filled Capillary. Analytical Chemistry. 2001; 73(18):4469-4477.

Rae, et al. Single-cell electroporation. Pflugers Arch. Eur J Physiol. Feb. 2002;443(4):664-70.

Sakmann, et al. Patch clamp techniques for studying ionic channels in excitable membranes. Annu Rev Physiol. 1984;46:455-72.

Seo, J., et al., Integrated Multiple Patch-Clamp Array Chip via Lateral Cell Trapping Junctions. Applied Physics Letters. 2004, 84(11):1973-1975.

Stett, et al. CYTOCENTERING: a novel technique enabling automated cell-by-cell patch clamping with the CYTOPATCH chip. Receptors Channels. 2003;9(1):59-66.

Stett, et al. Patch-clamping of primary cardiac cells with micro-openings in polyimide films. Med Biol Eng Comput. Mar. 2003;41(2):233-40.

Trapani, et al. Control of ion channel expression for patch clamp recordings using an inducible expression system in mammalian cell lines. Bmc Neuroscience. 2003; 4:15.

Tsong, T.Y. Electroporation of cell membranes. Biophysical Journal 1991; 60: 297-306.

Weaver, et al. Decreased bilayer stability due to transmembrane potentials. Phys Lett. 1981; 86A:57-59.

Weaver, J. C. Electroporation: a general phenomenon for manipulating cells and tissues. J Cell Biochem. Apr. 1993;51(4):426-35.

Wood, et al. Patch clamping by numbers. Drug Discov Today. May 15, 2004;9(10):434-41.

Xu, et al., Ion-channel assay technologies: quo vadis?. Drug Discovery Today. 2001: 6:1278-1287.

Office Action dated Jan. 17, 2011 regarding European Application No. 07759449.7.

Haas, et al. Single-cell electroporation for gene transfer in vivo. Neuron. Mar. 2001;29(3):583-91.

Klemic, et al., Micromolded PDMS planar electrode allows patch clamp electrical recordings from cells. Biosensors and Bioelectronics 2002, 17:597-604.

Weaver, et al. Theory of electroporation. In "Electroporation and Electrofusion in Cell Biology" (Neumann,E., Sowers, A., Jordan C, eds.). Plenum Press. New York. 1989; 111-126.

* cited by examiner

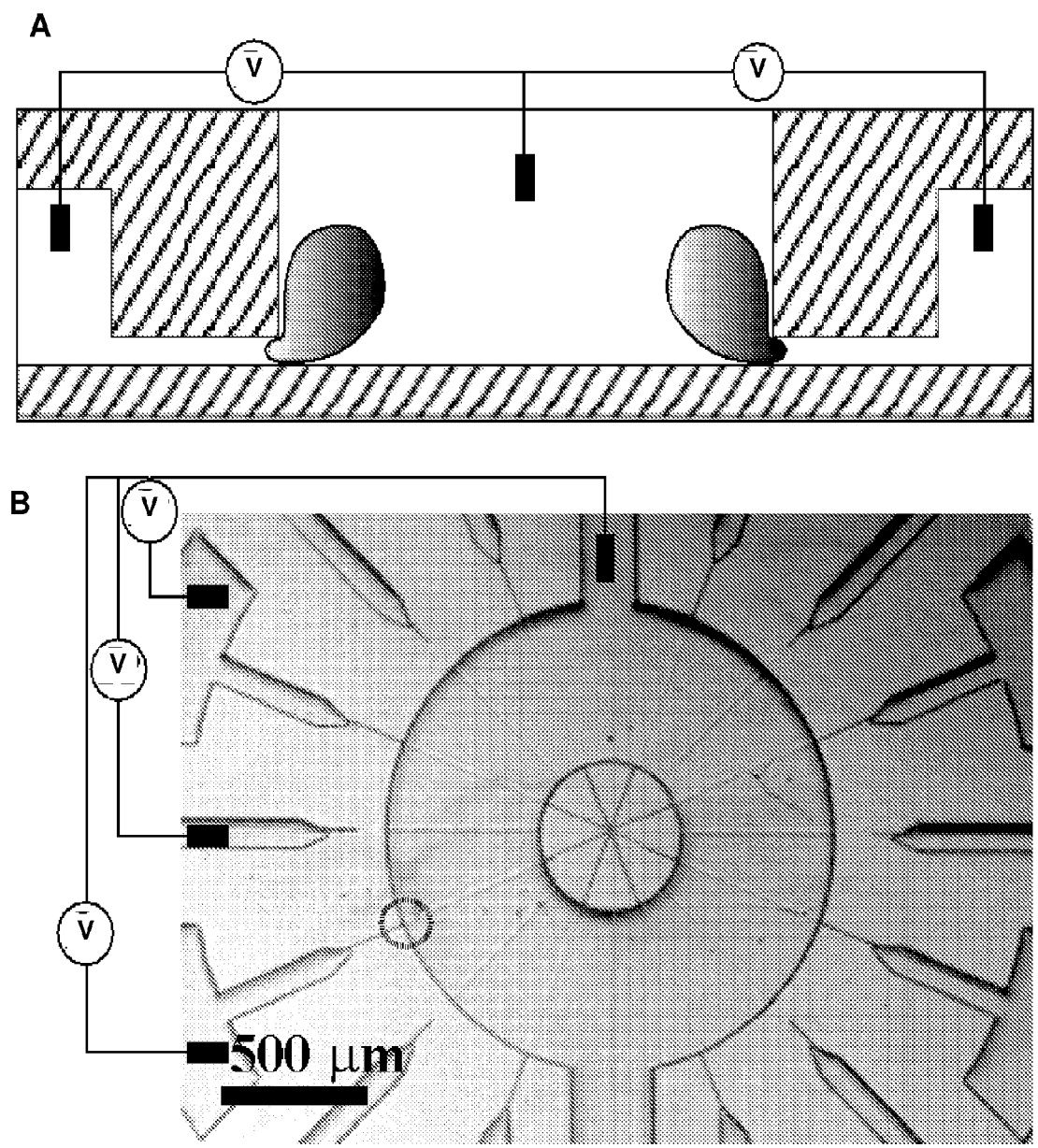
*FIG. 1A & B*

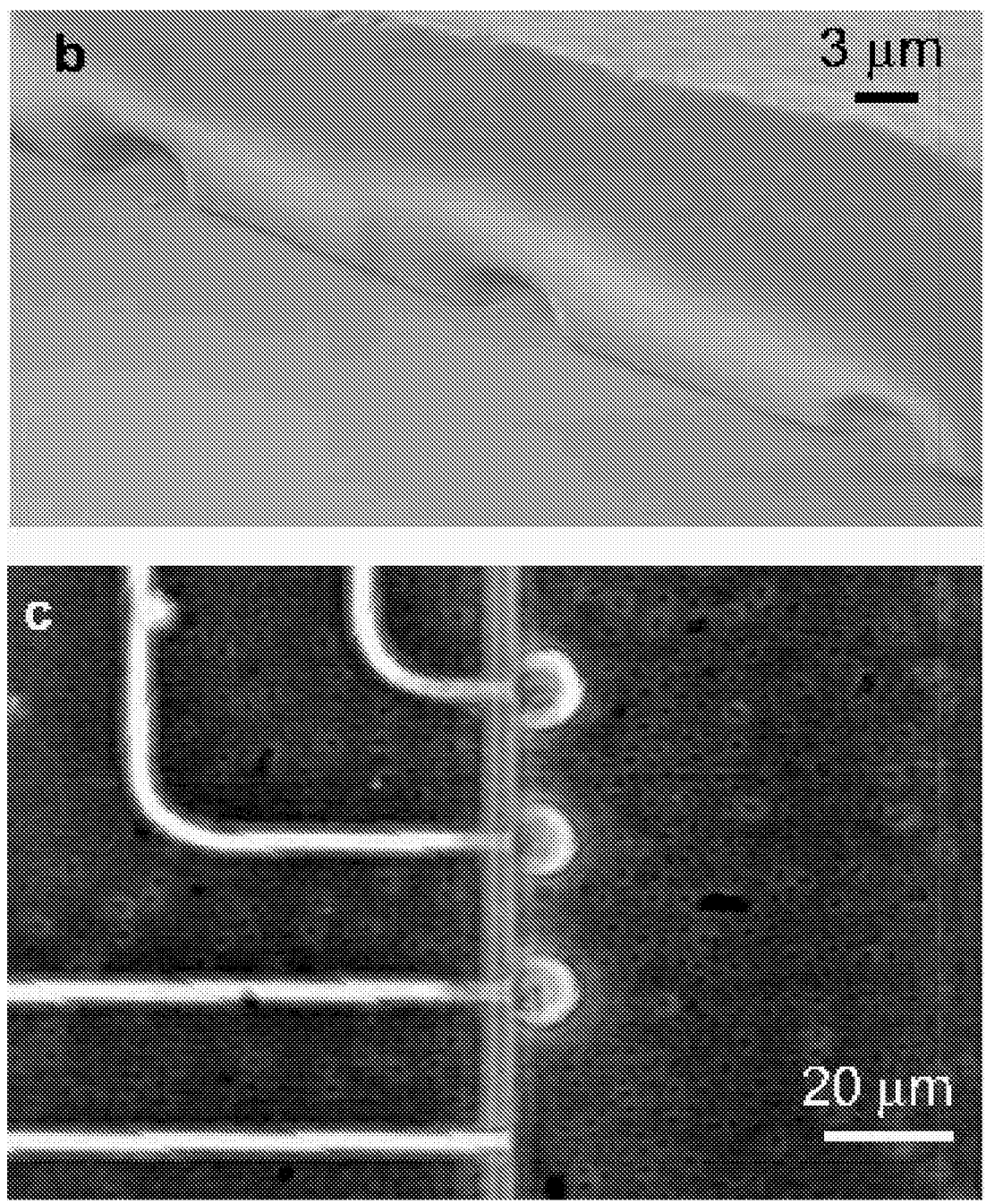
*FIG. 6B&C*

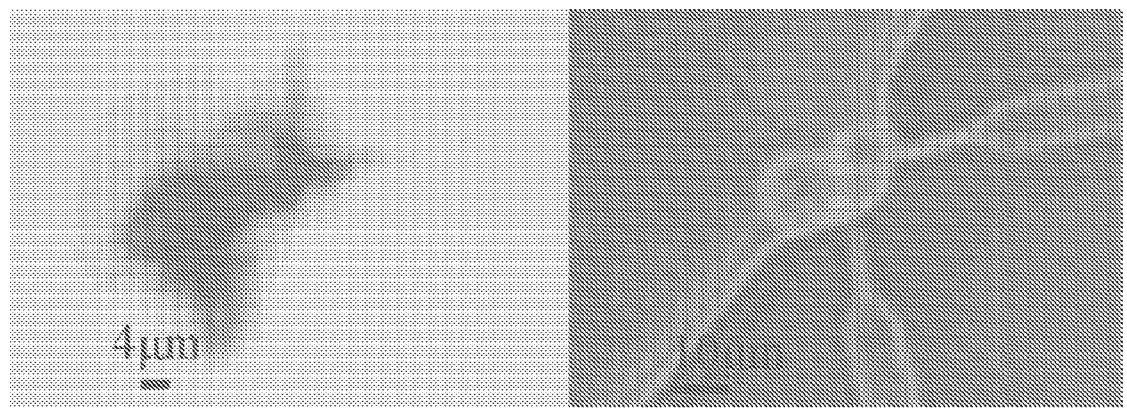
*FIG. 12A*   *FIG. 12B*

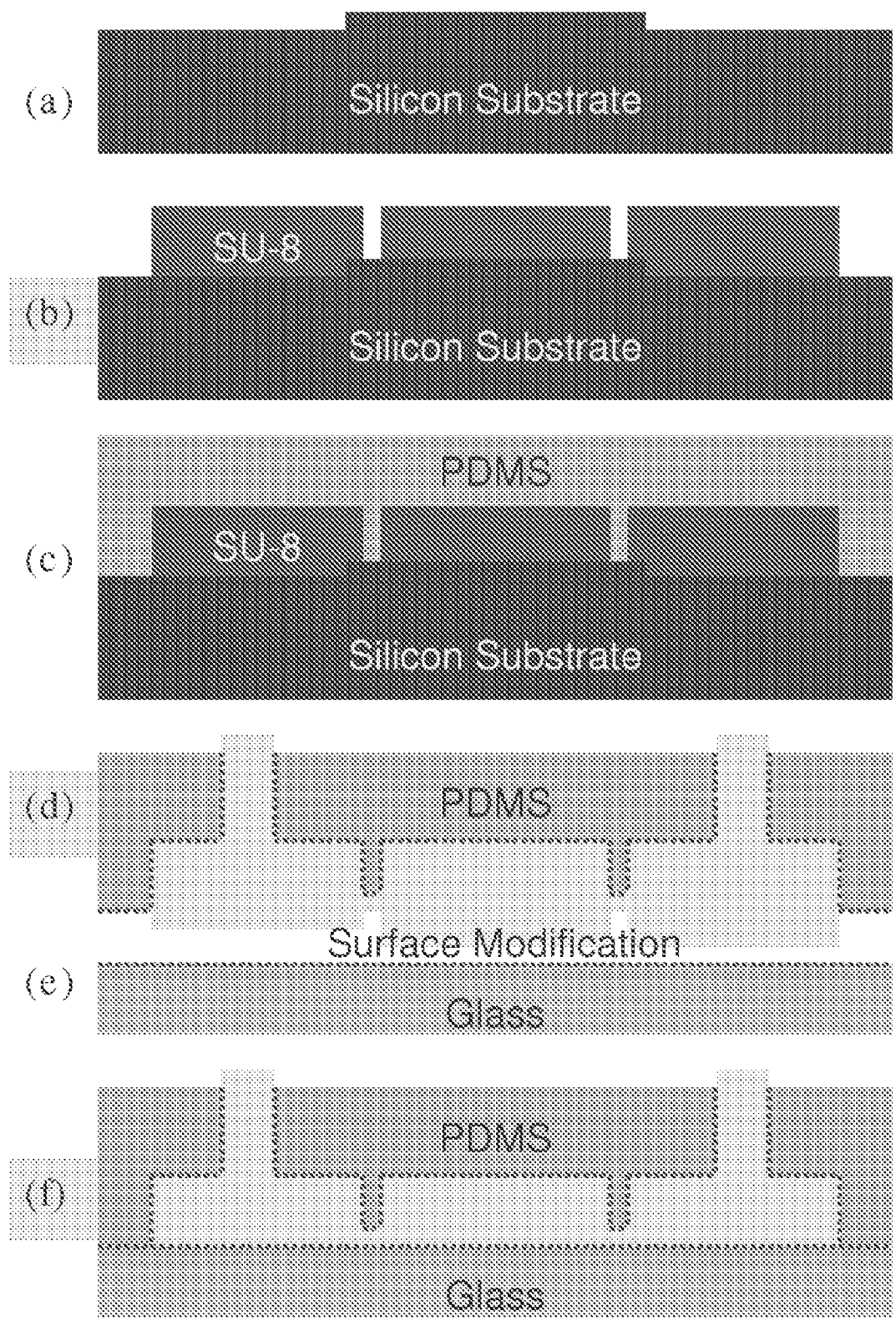
*FIG. 13 A-F*

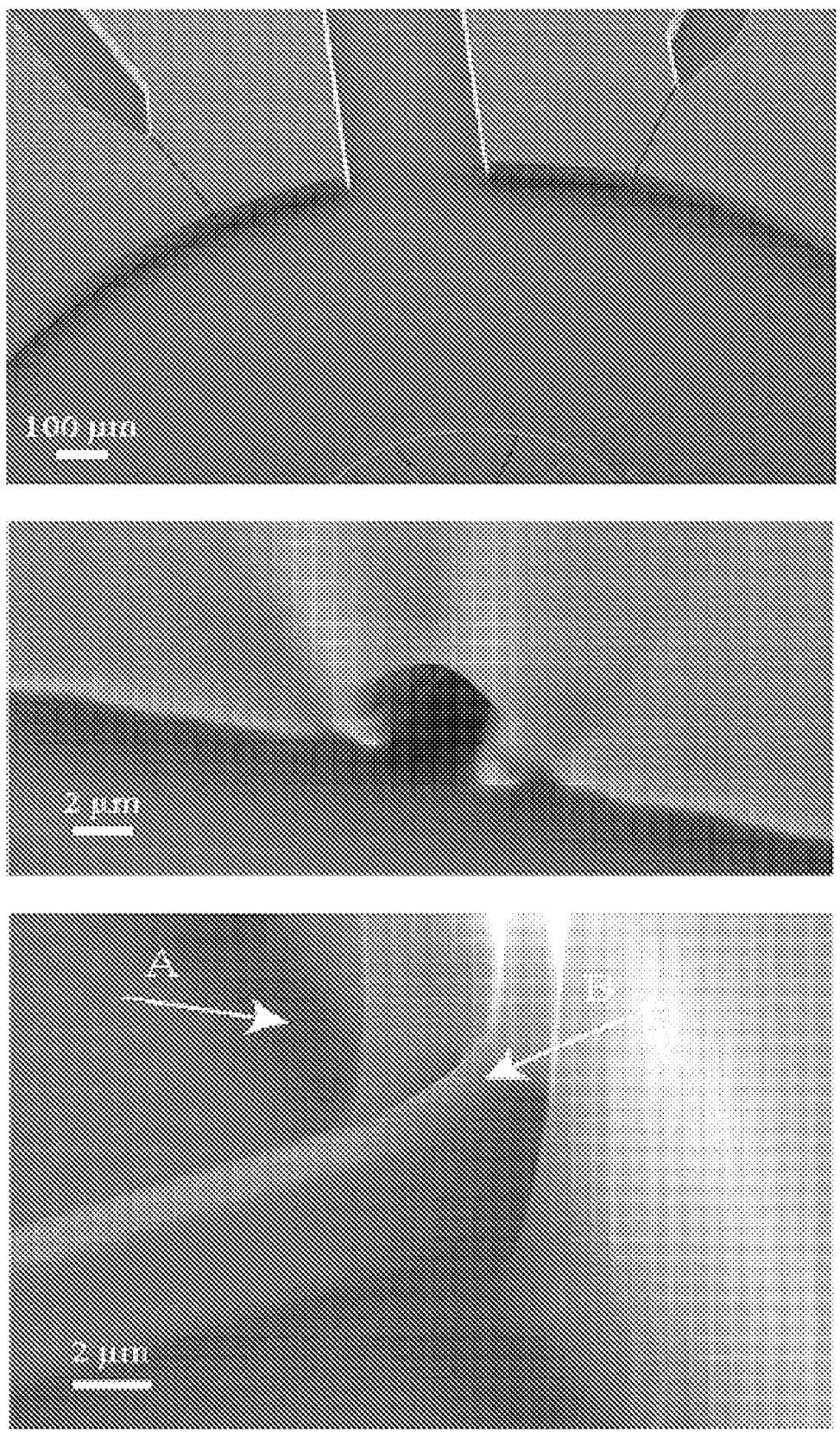
*FIG. 13 G&H&I*

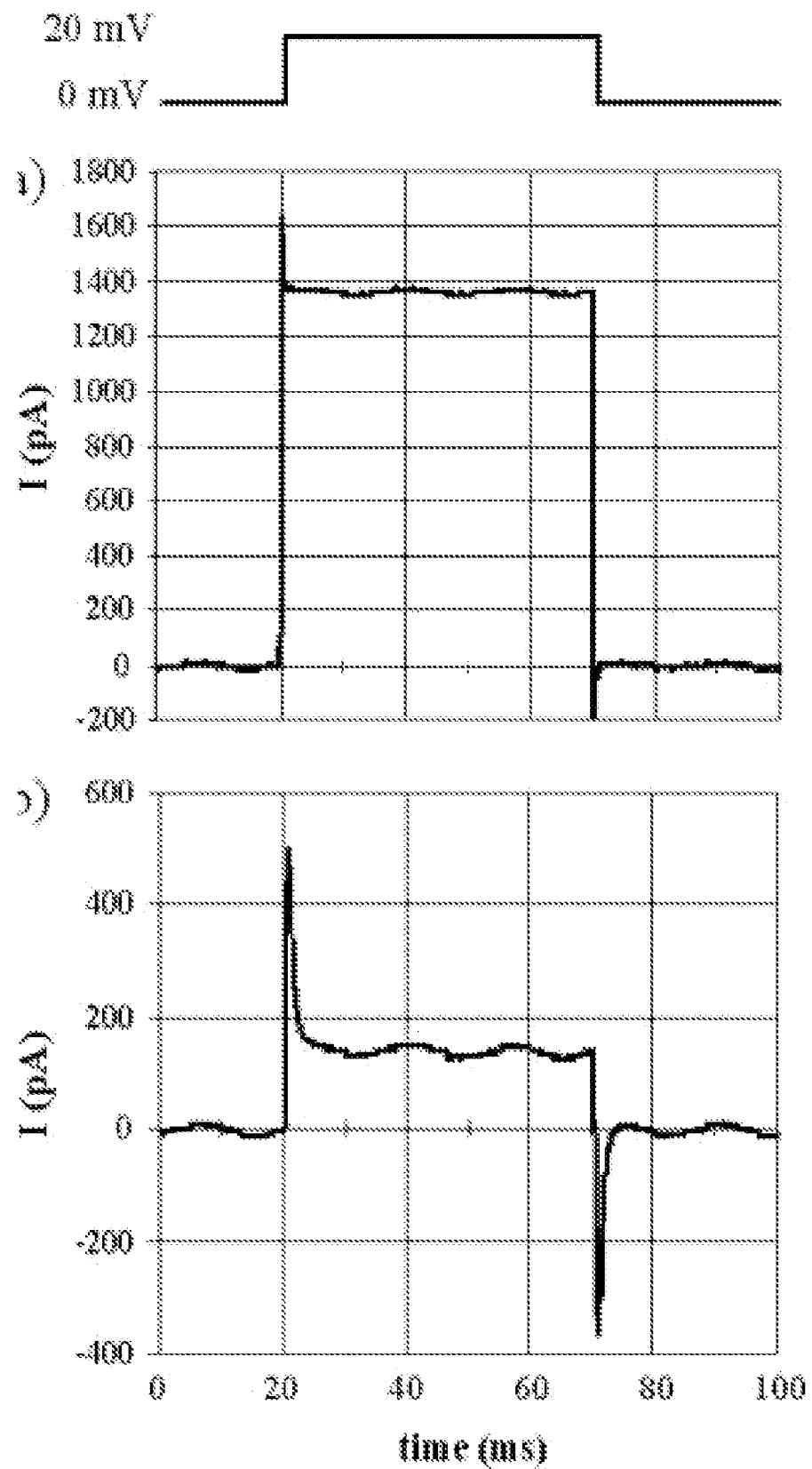
*FIG. 14A&B*

| Disease Classification | Disease |
|---|---|
| Cardiovascular Disease | Atherosclerosis; Unstable angina; Myocardial Infarction; Restenosis after angioplasty or other percutaneous intervention; Congestive Heart Failure; Myocarditis; Endocarditis; Endothelial Dysfunction; Cardiomyopathy |
| Endocrine Disease | Diabetes Mellitus I and II; Thyroiditis; Addisson's Disease |
| Infectious Disease | Hepatitis A, B, C, D, E; Malaria; Tuberculosis; HIV; Pneumocystis Carinii; Giardia; Toxoplasmosis; Lyme Disease; Rocky Mountain Spotted Fever; Cytomegalovirus; Epstein Barr Virus; Herpes Simplex Virus; Clostridium Dificile Colitis; Meningitis (all organisms); Pneumonia (all organisms); Urinary Tract Infection (all organisms); Infectious Diarrhea (all organisms) |
| Angiogenesis | Pathologic angiogenesis; Physiologic angiogenesis; Treatment induced angiogenesis |
| Inflammatory/Rheumatic Disease | Rheumatoid Arthritis; Systemic Lupus Erythematosis; Sjogrens Disease; CREST syndrome; Scleroderma; Ankylosing Spondylitis; Crohn's; Ulcerative Colitis; Primary Sclerosing Cholangitis; Appendicitis; Diverticulitis; Primary Biliary Sclerosis; Wegener's Granulomatosis; Polyarteritis nodosa; Whipple's Disease; Psoriasis; Microscopic Polyanngiitis; Takayasu's Disease; Kawasaki's Disease; Autoimmune hepatitis; Asthma; Churg-Strauss Disease; Beurger's Disease; Raynaud's Disease; Cholecystitis; Sarcoidosis; Asbestosis; Pneumoconioses |
| Transplant Rejection | Heart; Lung; Liver; Pancreas; Bowel; Bone Marrow; Stem Cell; Graft versus host disease; Transplant vasculopathy |
| Leukemia and Lymphoma | |

*FIG. 18. (TABLE 1)*

METHOD AND APPARATUS FOR INTEGRATED CELL HANDLING AND MEASUREMENTS

CROSS REFERENCE TO RELATED APPLICATIONS

This application claims priority from provisional patent application 60/710,305 filed 21 Aug. 2005 and is a continuation in part of PCT/US 2005/008349, filed 14 Mar. 2005, which claims priority from provisional patent application 60/552,892, filed 12 Mar. 2004, all incorporated herein by reference for all purposes.

COPYRIGHT NOTICE

Pursuant to 37 C.F.R. 1.71(e), applicants note that a portion of this disclosure contains material that is subject to copyright protection (such as, but not limited to, diagrams, device photographs, or any other aspects of this submission for which copyright protection is or may be available in any jurisdiction.). The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The present invention relates to methods and/or system and/or apparatus involving analysis and/or handling of cells and/or other biological material and that can be adapted to other applications. In specific embodiments, the invention involves methods and/or system and/or apparatus effective single cell electroporation using an efficient cell handling system or array.

BACKGROUND OF THE INVENTION

The discussion of any work, publications, sales, or activity anywhere in this submission, including in any documents submitted with this application, shall not be taken as an admission that any such work constitutes prior art. The discussion of any activity, work, or publication herein is not an admission that such activity, work, or publication existed or was known in any particular jurisdiction.

Handling, characterization, and visualization of individual cells has become increasingly valued in the fields of drug discovery, disease diagnoses and analysis, and a variety of other therapeutic and experimental work. However, few high-resolution methods exist to control and manipulate the biochemical nature of a single cell's interior; yet roughly 90% of the cell's biologically active structures, such as intracellular proteins, are located within the confines of the cell membrane. The cell membrane serves as an effective barrier between the cytoplasm and the outside world and, as such, is relatively impermeable to most ionic and polar substances.

One way to and access the cell's interior is by temporarily increasing the cell membrane's permeability. This can be accomplished via electroporation, a technique using high electric fields to induce structural rearrangements of the cell membrane. Pores are formed when the transmembrane potential exceeds the dielectric break-down voltage of the membrane (about 0.2-1.5V). Material such as polar substances other-wise impermeant to the plasma membrane (such as dyes, drugs, DNA, proteins, peptides, and amino acids) can thus be introduced into the cell.

In the early 1980s, Eberhard Neumann et al. demonstrated the feasibility of electroporation for delivering DNA to a population of mammalian cells. Since then, methods of bulk electroporation has become a standard technique routinely used to simultaneously transfect millions of cells in culture. However, bulk electroporation requires very high voltages ($>10^3$V) and has little control over the permeabilization of individual cells, resulting in suboptimal parameters. Reversible electroporation, in which the pores can reseal, is therefore difficult.

While single cell electroporation has been hoped to have advantages over bulk methods, practical systems or methods for single cell electroporation have generally been less commonly used than bulk methods. Lundqvist et al. first demonstrated single cell electroporation using carbon fiber microelectrodes in 1998. To induce electroporation, they placed the microelectrodes 2-5 microns away from adherent progenitor cells. Other single cell electroporation techniques developed since include: electrolyte-filled capillaries, micropipettes, and microfabricated chips.

In 2001, Huang et al. introduced a microfabricated single cell electroporation chip. In 2002, Nolkrantz et al. demonstrated functional screening of intracellular proteins by using electroporation to introduce fluorogenic enzyme substrates and receptor ligands into single cells.

Chip-based cellular handling devices have been proposed using silicon oxide coated nitride membranes, silicon elastomers, polyimide films, quartz or glass substrates. Recently, three dimensional structures more similar to patch pipettes have also been fabricated. Some earlier chip-based devices developed to date generally use a horizontal geometry where the patch pore is etched in a horizontal membrane dividing the top cell compartment from the recording electrode compartment.

The following are incorporated herein by reference to provide background.

1. J. A. Lundqvist, F. Sahlin, M. A. Aberg, A. Strimberg, P. S. Eriksson and O. Orwar, *Proc. Natl. Acad. Sci.*, 95, 10356-10360 (1998).
2. K. Nolkrantz, C. Farre, A. Brederlau, I. D. Karlsson, C. Brennan, P. S. Eriksson, S. G. Weber, M. Sandberg and O. Orwar, *Anal. Chem.*, 73(18), 4469-4477(2001).
3. K. Haas, W. C. Sin, A. Javaherian, Z. Li and H. T. Cline, *Neuron*, 29, 583-591 (2001).
4. Y. Huang and B. Rubinsky, *Sens. Actuators*, A, 89, 242-249 (2001).
5. T. Y. Tsong, Biophysical Journal, 1991, 60, 297-306.
6. J. C. Weaver, J.Cell Biochem, 2002, 51,426-435.
7. J. L. Rae, R. A. Levis. Eur J Physiol.2002,443,664-670.
8. I. G. Abidor, V. B. Arakelyan, L. V. Chernomordik, Y. A Chizmadzhec, V. F. Patushenko, M. R. Tarasevich, Bioelectrochem. Bioenerg. 1979, 6, 37-52.
9. J. C. Weaver and K. T. Powell, in "Electroporation and Electrofusion in Cell Biology" (Neumann,E., Sowers, A., Jordan C, eds.) pp 111-126. Plenum Press. New York.
10. Weaver, J. C., and Mintzer, R. A. Decreased bilayer stability due to transmembrane potentials. Phys Lett., 1981, 86A, 57-59.
11. E.Neumann, M. Schaefer-Ridder, Y. Wang, P. H. Hofschneider,EMBO J, 1982,1,841-845.
12. D. C. Chang, B. M. Chassy, J. A. Saunders, A. E. Sowers, "Guide to Electroporation and Electrofusion". Academic Press, Inc. 1992. San Diego.
13. K. Nolkrantz, C. Farre, A. Brederlau, R., I. D. Karlsson, C. Brennan, P. S. Eriksson, S. G. Weber, M.Sandberg, O. Orwar, O. Anal. Chem, 2001; 73(18); 4469-4477.

14. J. Seo, C. Ionescu-Zanetti, J. Diamond, J., R. La, L. P. Lee, Applied Physics Letter,2004, 84,11:1973-1975.
15. E. Neumann, K. Toensing, S. Kakorin, P. Budde, and J. Frey, Biophys J, 1998, 74, 98-108.
16. D. Needham and R. M. Hochmuth, Biophys J., 1989, 55, 100 1-1009.
17. J. Akinlaja and F. Sachs, Biophys J., 1998, 75, 247-254.

SUMMARY

The present invention, in specific embodiments, involves methods and or devices that provide improved cellular handling in particular to enable single cell electroporation. In other embodiments the invention involves systems for multiple single-cell electroporation and/or electrofusion of cells with other cells or vesicles. In general, the invention accomplishes successful single cell electroporation by generally both isolating the cell and providing a well focused electric field through the device configuration. In specific embodiments, a device according to the invention can selectively trap targeted cells and focus an electric field for: reversible electroporation (in which the pores reseal), intracellular perfusion, and/or cell fusion.

Specific embodiments involve lateral cell trapping junctions at a micron scale, integrated with microfluidic channels wherein cell immobilization or trapping pores generally are arranged as openings in a sidewall or analogous structure of a main fluidic channel. At times herein, this cell trapping structure is referred to as a lateral pore or junction. In specific embodiments, microfabricated devices according to the invention can be ideally suited to both isolate single cells and focus an electric field for cell electroporation. Microfabrication technology according to specific embodiments of the invention also enables the incorporation of other functionalities onto devices of the invention. The invention thus can enable a comprehensive screening device that can not only permeate single cells—but also introduce materials into the cell and monitor its response. In further embodiments, the invention involves a device or system able to introduce otherwise impermeable compounds such as dyes, drugs, or DNA into cells.

In further embodiments, the invention involves a PDMS based platform able to create a transmembrane potential across a cell using low voltages such that dielectric breakdown of the membrane is achieved. In particular embodiments, the invention applies a low voltage (<about 1 Volt) to create a large potential drop (of about 750 V/cm) across the cell membrane. In response to this transmembrane potential, dielectric breakdown of the membrane is achieved and cell membrane phospholipids can rearrange to create transient pores. These pores allow compounds to be delivered into the cell, for example via an integrated capillary channels or a backside perfusion channel. In alternative embodiments, cells can also be fused with each other or with pre-loaded vesicles for volume controlled intracellular delivery using electrofusion.

The present invention, in further embodiments, involves an integrated multiple cellular handling array system or device that utilize lateral cell trapping junctions to enable electroporation and/or electrofusion and associated electrical measurements. In specific example systems, the intersectional design of a microfluidic network provides multiple cell addressing and manipulation sites for efficient electrophysiological measurements and cell manipulations at a number of sites.

In specific embodiments, a device of the invention provides and also allows for visual observation of membrane deformation. In specific embodiments, device fabrication is based on micromolding of one or more elastomers (such as, polydimethylsiloxane (PDMS)), allowing for inexpensive mass production of disposable high-throughput biochips. Other embodiments can be constructed from bonded silicon/polysilicon surfaces or injection molded polymers.

The lateral design according to some specific embodiments of the invention also allows for construction of systems having efficient multiplexing of measurements, exchange of intracellular and extracellular electrolyte while the cell is attached to a pore, and optical observation of membrane deformation and cellular content. Thus, in specific embodiments, the invention enables high throughput, low cost systems allowing for cell electroporation, electrofusion and other cellular manipulations and/or assays.

The lateral design according to some specific embodiments of the invention also allows for construction of systems having efficient multiplexing of measurements, exchange of intracellular and extracellular electrolyte while the cell is attached to the pore, and optical observation of membrane deformation and cellular content. Thus, in specific embodiments, the invention enables high throughput, low cost cell-based patch clamp measurements and other cellular manipulations and/or assays.

According to specific embodiments of the invention, aspects of the invention can be incorporated into one or more integrated systems that provide simple yet elegant means for trapping multiple cells instantaneously by pneumatic controls and allows simultaneous electrical and optical characterizations, providing an ideal mechanism for high throughput screening (HTS) single cells analysis and drug discovery.

In further specific embodiments, the novel methods and devices according to specific embodiments of the invention can be used in various micrometer systems. Applications include BioMEMS, lab on a chip, cell-based assays, etc.

Other Features & Benefits

The invention and various specific aspects and embodiments will be better understood with reference to drawings and detailed descriptions provided in this submission. For purposes of clarity, this discussion refers to devices, methods, and concepts in terms of specific examples. However, the invention and aspects thereof may have applications to a variety of types of devices and systems. It is therefore intended that the invention not be limited except as provided in the attached claims and equivalents.

Furthermore, it is well known in the art that systems and methods such as described herein can include a variety of different components and different functions in a modular fashion. Different embodiments of the invention can include different mixtures of elements and functions and may group various functions as parts of various elements. For purposes of clarity, the invention is described in terms of systems that include many different innovative components and innovative combinations of innovative components and known components. No inference should be taken to limit the invention to combinations containing all of the innovative components listed in any illustrative embodiment in this specification.

In some of the drawings and detailed descriptions below, the present invention is described in terms of the important independent embodiment of a biologic assay and/or array system and components thereof. This should not be taken to limit the invention, which, using the teachings provided herein, can be applied to a number of other situations.

In some of the drawings and detailed descriptions below, the present invention is described in terms of a number of specific example embodiments including specific parameters related to dimensions of structures, pressures or volumes of liquids, or electrical values. Except where so provided in the attached claims, these parameters are provided as examples and do not limit the invention to other devices or systems with different dimensions.

All references, publications, patents, and patent applications cited in this submission are hereby incorporated by reference in their entirety for all purposes.

BRIEF DESCRIPTION OF THE DRAWINGS

FIG. 1A-D illustrate example aspects of cell manipulation devices according to various embodiments of the invention.

FIG. 6A-C illustrate aspects of an example integrated cellular manipulation array on a microfluidic platform according to specific embodiments of the invention.

FIG. 12A-B are micrographs illustrating electrofusion of two cells (A) and two vesicles (B) according to specific embodiments of the invention.

FIG. 13A-I illustrate an example of aspects of fabrication of a device array according to specific embodiments of the invention.

FIG. 14A-B illustrate current response to a 20 mV voltage pulse before (a) and after (b) cell trapping of an example device according to specific embodiments of the invention.

FIG. 18 (Table 1) illustrates an example of diseases, conditions, or statuses that can evaluated or for which drugs or other therapies can be tested according to specific embodiments of the present invention.

DESCRIPTION OF SPECIFIC EMBODIMENTS

1. Overview

Figure 1C:
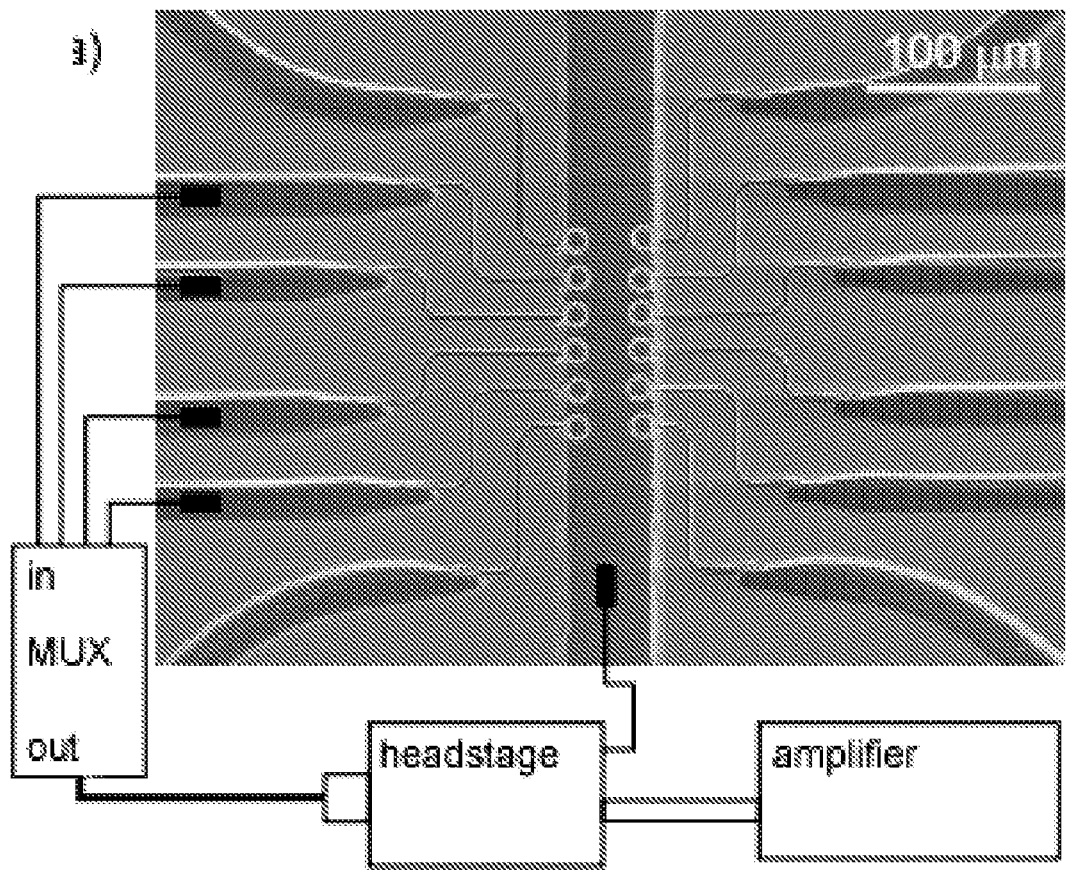

The present invention, according to various specific embodiments as described herein, provides methods, systems, and devices that allow for very dense integration of cell handling and microfluidic control in an integrated platform and that allow for inexpensive manufacture, easy of visualization, and other advantageous as will be apparent from the descriptions herein. In specific embodiments, the invention is involved with efficient systems and methods for cell electroporation and/or electrofusion.

In general, electroporation occurs when a cell's transmembrane potential exceeds the dielectric breakdown potential of the membrane, typically reported to be about 0.2-1.5V In specific devices according to the invention an electric field is applied across a cell held using a trapping pore and with Ag/AgCl (or other conductor) electrodes electrically connected to channels on either side of the cell. With a trapping channel made from a good electrical insulator (e.g., polydimethysiloxane (PDMS)), the electric field can be focused such that the greatest potential drop occurs first across the portion of the cell membrane within the trapping channel (e.g., 3.1 µm×4 µm in specific embodiments). As resistance is inversely proportional to surface area, and the surface area of the first membrane is <100× that of the membrane outside the trapping site, the resistance of the first membrane is significantly larger than the other membrane. Therefore the critical transmembrane potential—and thus electroporation—occurs here first. In further embodiments, after this portion of the membrane porates and its resistance decreases, the other side of the cell porates and cell fusion is achievable with the abutting cell.

2. Example Device Configurations

FIG. 1A-D illustrate example aspects of cell manipulation devices according to various embodiments of the invention. Each of the examples shows lateral cell trapping junctions according to specific embodiments of the invention. With the pores in the horizontal plane, closely spaced (only about 10-20 microns apart) multiplexed parallel sites are possible. Drugs, reagents, or other material can therefore be administered in small volumes, while operation of the device can be recorded and/or viewed in parallel at a number of sites. In various example fabrications, the whole device is fabricated using micromolding of an elastomer such as polydimethylsiloxane (PDMS), a high-throughput, inexpensive procedure.

More specifically, FIG. 1A is a schematic diagram showing in cross-section two lateral cell trapping pores or junctions on the sides of a central channel. In this and other figures herein, specific examples are shown wherein a narrow trapping fluidic connection operatively connects to the lateral pore. A larger fluidic connection or reservoir is provided at the other end of the narrow trapping connection (or channel) to allow easier fluidic access. Such trapping connections and pores can be configured in a circular central channel, a curved central channel, or a roughly linear central channel, as described elsewhere herein. Spacing between pores and the dimensions of elements can be varied, as will be understood to those of skill in the art from the teachings described herein.

FIG. 1B is a top view micrograph of an example device showing a circular central channel with 14 radial cell trapping pores. Each trapping pore is connected by a narrow trapping channel to a fluidic reservoir that can be connected to other microfluidic controls on the device as described elsewhere herein. In this example, two larger channels that can be used for ingress or egress of cells, fluids, or other materials connect to the central channel. There are fourteen small channels illustrated in this example (though only eight are opened in this particular chip) for cell trapping. Operational electrical connectivity of electrodes in one of the ingress/egress channels and three trapping connections is shown schematically in the figure. The small circle at the lower left indicates one of the lateral capture sites. In this design, cell pores are radially about 200 microns apart, as shown by the dimensional bar. This dimension is an example only, and much smaller versions of this same design can also be constructed.

FIG. 1C is a top view micrograph of an example higher density device showing a roughly linear main channel, and 12 trapping pores and connected trapping channels that are about 20 microns (μm) apart or less. Again, optional electrical connectivity is schematically shown. In this figure, the 12 circular diagrams indicate locations of trapped cells at the lateral trapping junctions.

Figure 1D:
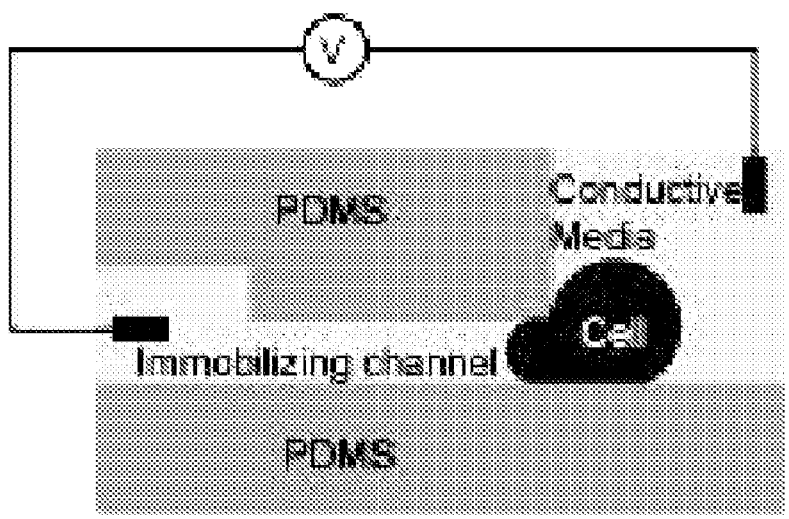

FIG. 1D is a schematic showing and alternative cross-sectional side view. When is trapped, a cell is pulled laterally into the small trap-ping channel by applying a negative pressure. The trapped cell acts as a high resistance component in the circuit.

Figure 2:
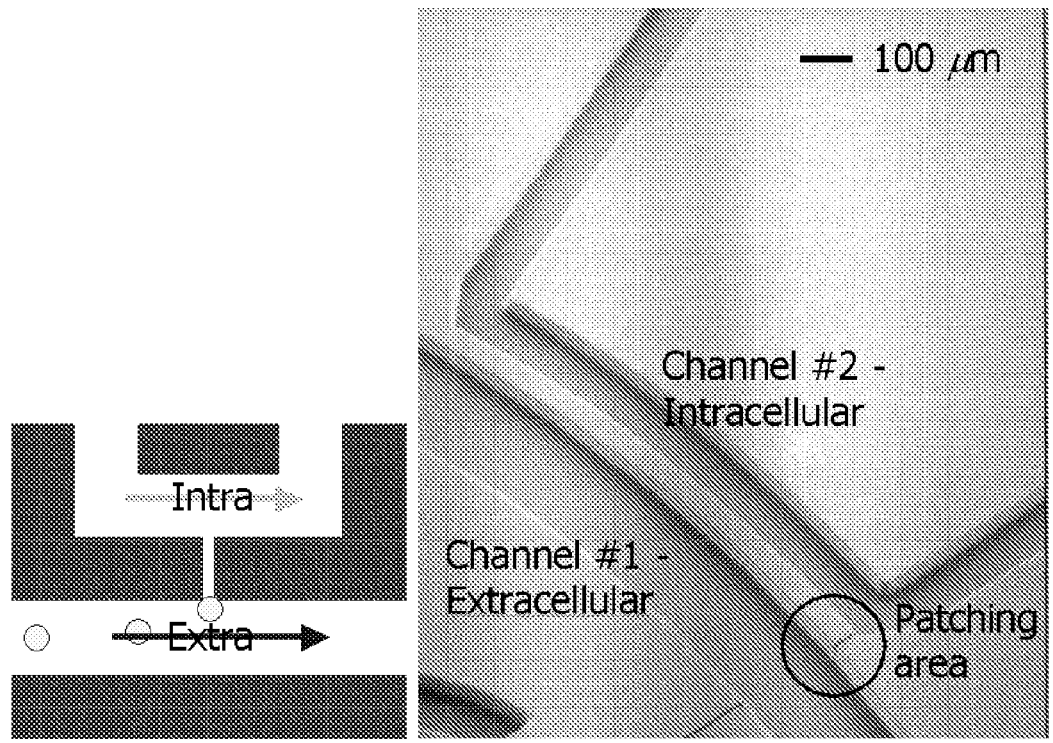
FIG. 2 illustrates aspects of an example double channel device allowing for rapid change of intracellular and extracellular solutions according to alternative specific embodiments of the invention.

FIG. 2 illustrates aspects of an example double channel device allowing for rapid change of intracellular and extracellular solutions according to alternative specific embodiments of the invention. In this alternative design, negative pressure can be maintained in the intracellular channel with respect to the extracellular channel to cell trapping, while the two separated channels allow rapid exchange of fluids in either channel. This type of trapping junction can be incorporated in various designs as will be understood from the teachings provided herein.

Figure 3:
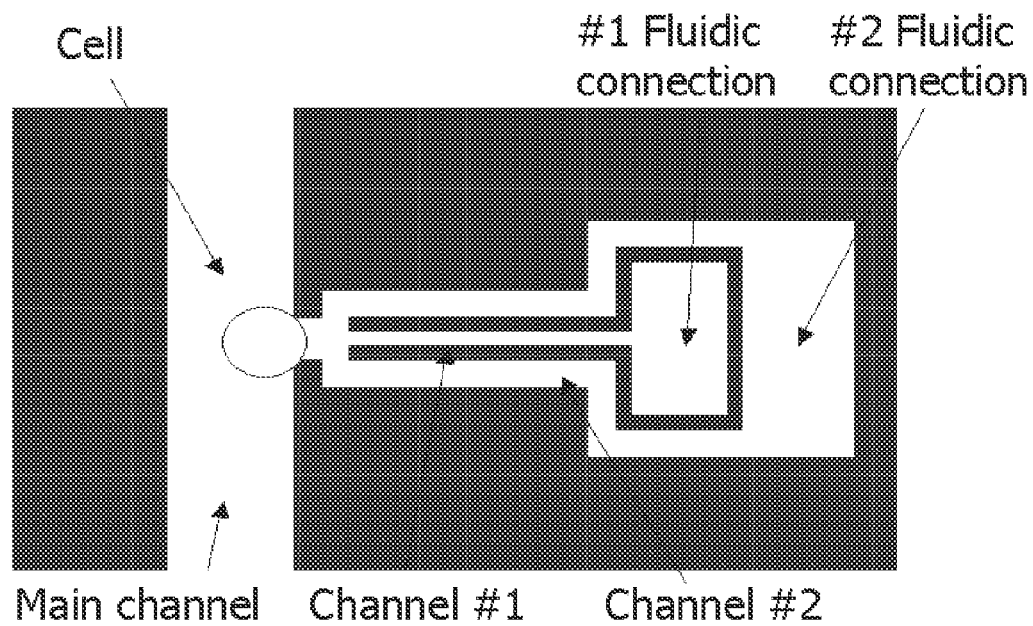
FIG. 3 illustrates an example of a simple lateral junction cell trapping disposable concentric device according to alternative specific embodiments of the invention.

FIG. 3 illustrates an example of a simple lateral junction cell trapping disposable concentric device according to alternative specific embodiments of the invention. This is a further alternative configuration showing two fluidic connections for the intracellular area, allowing for fast fluidic exchange and providing a very simple immobilization area for cell electroporation. In particular example embodiments, a device such as shown in FIG. 3 or in any of the other figures can be incorporated into various cell handling or lab-on-a-chip systems that may incorporate many other handling steps of structures.

3. Pore Configurations

FIG. 4 and FIG. 5 are close-up micrographs showing aspects of cell trapping pores according to specific embodiments of the invention. In each of these figures, a different geometry opening is presented to the cellular area for effecting cell trapping. Either of these cell trappings junctions or other junction configurations including semi-circular capture areas can be incorporated into devices according to specific embodiments of the invention as an alternative to the straight lateral capture pore illustrated in other examples provided herein. Different configurations may provide better trapping and/or sealing in particular situations.

Figure 4A:
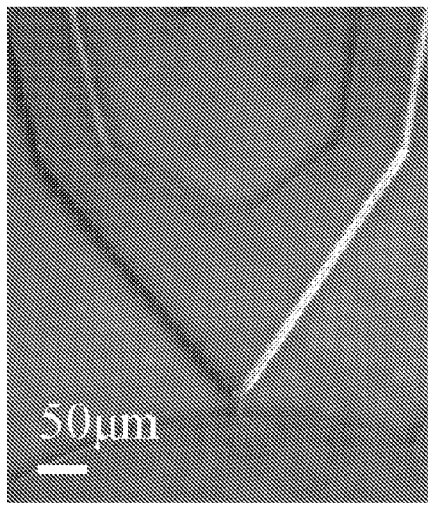
FIG. 4A-B illustrate geometries for an opening to a lateral cell trapping junction particularly suited for electroporation and/or electrofusion according to specific embodiments of the invention.
Figure 4B:
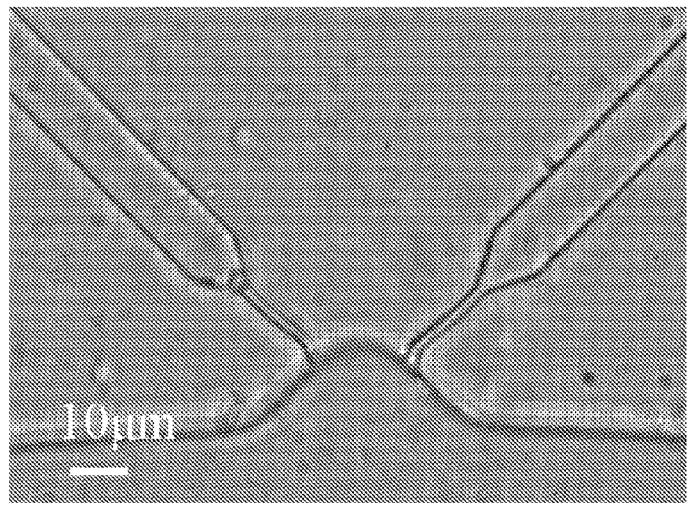

FIG. 4A-B illustrate geometries for an opening to a lateral cell trapping junction particularly suited for electroporation and/or electrofusion according to specific embodiments of the invention. FIG. 4A is a micrograph illustrating an electroporation/backside perfusion connection and a cell trapping poor in which an electrode can be configured in one end of a Y shaped channel. FIG. 4B illustrates a configuration wherein two cell trapping pores are closely spaced, in this example within an indentation off of the mail cell transport channel, to allow the immobilization of either two cells; a cell and a vesicle; or two vesicles in a position convenient for eletrofusion.

Figure 5A:
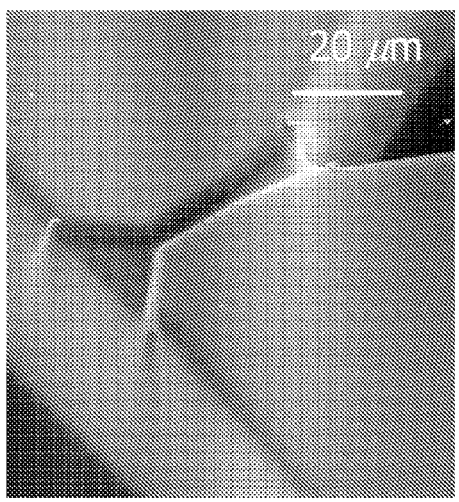
FIG. 5A-B illustrate optional different geometries for an opening to a lateral cell junction according to specific embodiments of the invention.
Figure 5B:
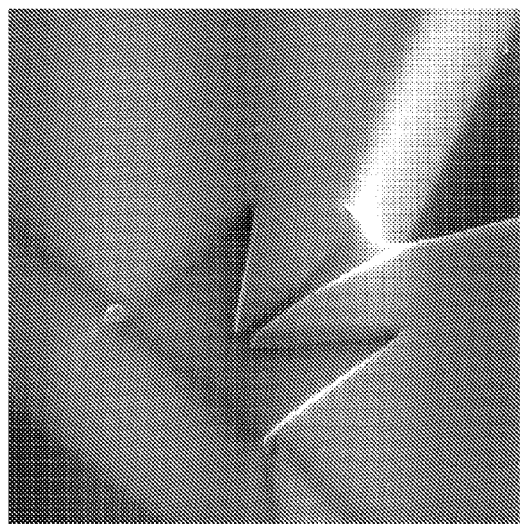

FIG. 5A-B illustrate optional different geometries for an opening to a lateral cell junction according to specific embodiments of the invention.

4. Example Integrated Cell Manipulation System

In further embodiments, a high-density integrated cell handling system provides improves visualization and control of cell position allowing the integration of whole cell electrophysiology with easily manufactured microfluidic lab-on-a-chip devices. As described elsewhere herein, devices of the invention can be fabricated by micromolding of polydimethylsiloxane (PDMS) or materials with similar or analogous properties. In specific embodiments, holding a cell at a pore at an integrated substrate eliminates the need for vibration isolation and allows for more precise electric focus as compared to other methods. The present invention in specific embodiments achieves this even with very dense pore placement. According to specific embodiments, a cell manipulation device of the invention also allows direct cell visualization including of multiple cells and using standard microscopy.

In specific embodiments of the invention, microfluidic integration allows capillaries to be arrayed about less than 10-30 microns apart, for a total chamber volume of less than about 0.5 nanoliters. The geometry of cell pores and fluidic connection in specific embodiments permits high quality, stable, whole-cell seals despite the hydrophobicity of some surfaces, such as PDMS. In particular embodiments, the lateral geometry of the trapping junctions in combinations with the long, thin trapping channels as shown provides great surface area allowing for a more stable seal.

Replacing silicon micromachining with PDMS micromolding has a number of advantages, among which, the fabrication is sufficiently simple (requiring only molding and bonding) and economical to enable the production of single use disposable devices. Further, unlike silicon based devices, the PDMS device is transparent and can be bonded to a 12 mm glass coverslip, permitting placement on the stage of an inverted microscope and visualization of cells during recording.

Figure 6A:
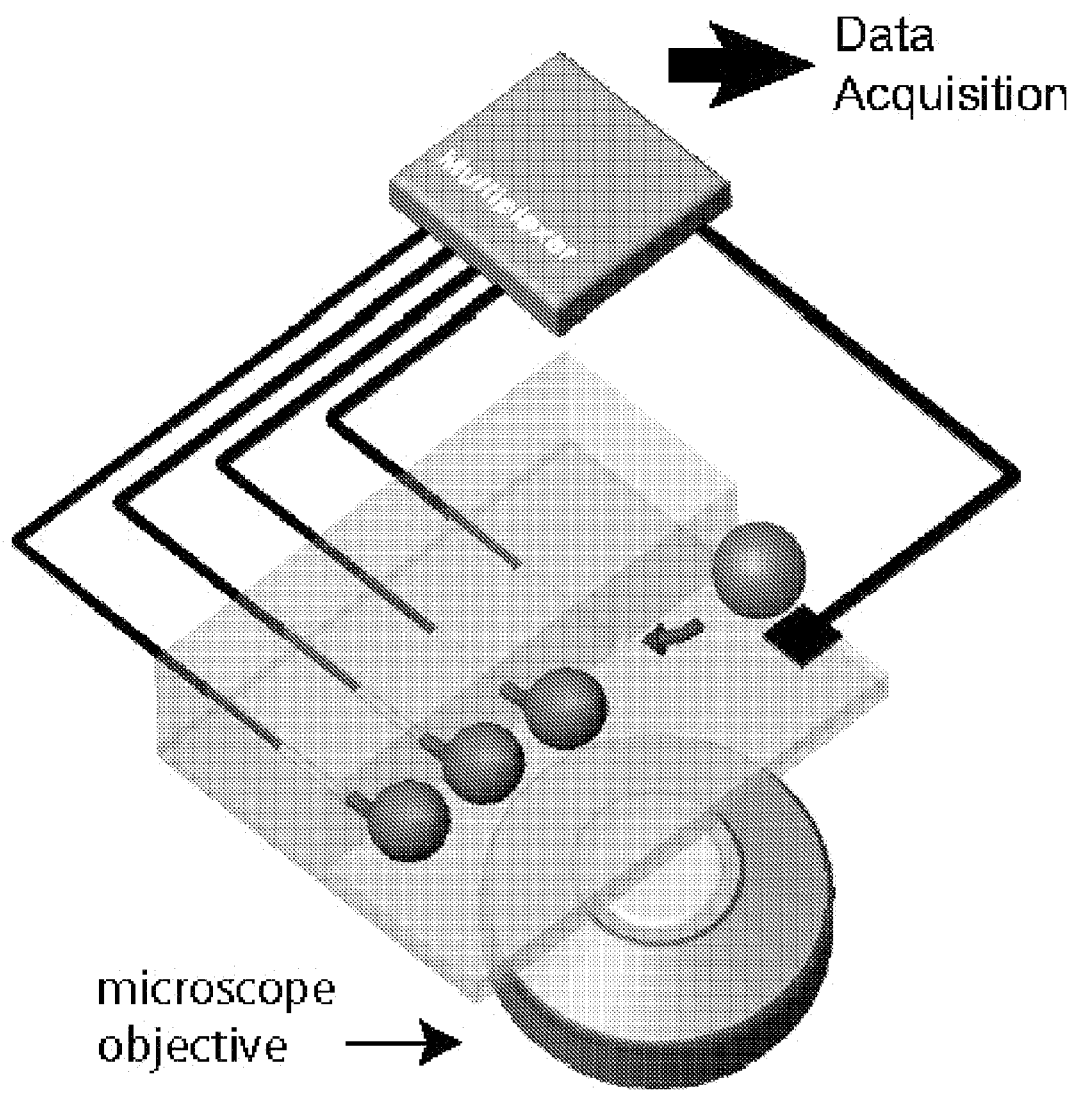

FIG. 6A-C illustrate aspects of an example integrated cellular manipulation array on a microfluidic platform according to specific embodiments of the invention. As above, cell trapping is achieved by applying negative pressure to trapping connection capillaries which open into a main chamber containing cells in suspension, which are represented schematically as spheres in FIG. 6A. Attached cells deform, protruding into the capillaries.

Where desired, electroporation, electrofusion, and/or electrical monitoring is enabled by connecting electrodes (such as the AgCl electrodes described herein) in each of the capillaries, as well as the main chamber. Signals are fed through a multiplexing circuit and into the data acquisition system (multiplexer setup and microscope objective not to scale). The device can be bonded to a glass coverslip for optical monitoring.

FIG. 6B is a scanning electron micrograph of three recording capillary orifices as seen from a main chamber of a cell manipulation system according to specific embodiments of the invention. Example capillary cross-section dimensions are 4 μm×3 μm, with a pore-to-pore (or site-to-site) distance of about 20 μm.

FIG. 6C is a darkfield optical microscope image of cells trapped at three capillary orifices. An example device having 12 capillaries arrayed six along each side of the main chamber fluidic channel, along a 120 μm distance is shown in the micrograph of FIG. 1C.

In this example configuration, cell trapping was confirmed by light microscopy. The cells are placed in suspension in the central chamber and are sequentially brought to the patch pores by applying negative pressure (28 kPa) to the patch capillaries. In an example system, the total time required for trapping is under three seconds per cell. Trapped cells (shown schematically in FIG. 6A) can be visualized using dark field microscopy as seen in FIG. 6C.

In an array according to specific embodiments of the invention, the recording lo capillary and the cell substrate are mechanically bonded, eliminating the need for external positioning devices and minimizing the effects of ambient vibration. Early testing has confirmed that seals last for more than about 20-40 min even without the use of vibration isolation equipment, though it is expected that longer seal times can be achieved.

Advantageous features of this design are inherent microfluidic integration, very high density of cell trapping sites, and the ability to measure both cell deformation and membrane integrity.

As a further improvement to a microfluidics based lateral geometry for electrical measurements of cells, the average seal resistance is increased to provide better electrical characteristics, for example by partial cure bonding of the elastomer, which results in improvement in cell attached seal resistance to the gigaohm range.

Figure 7:
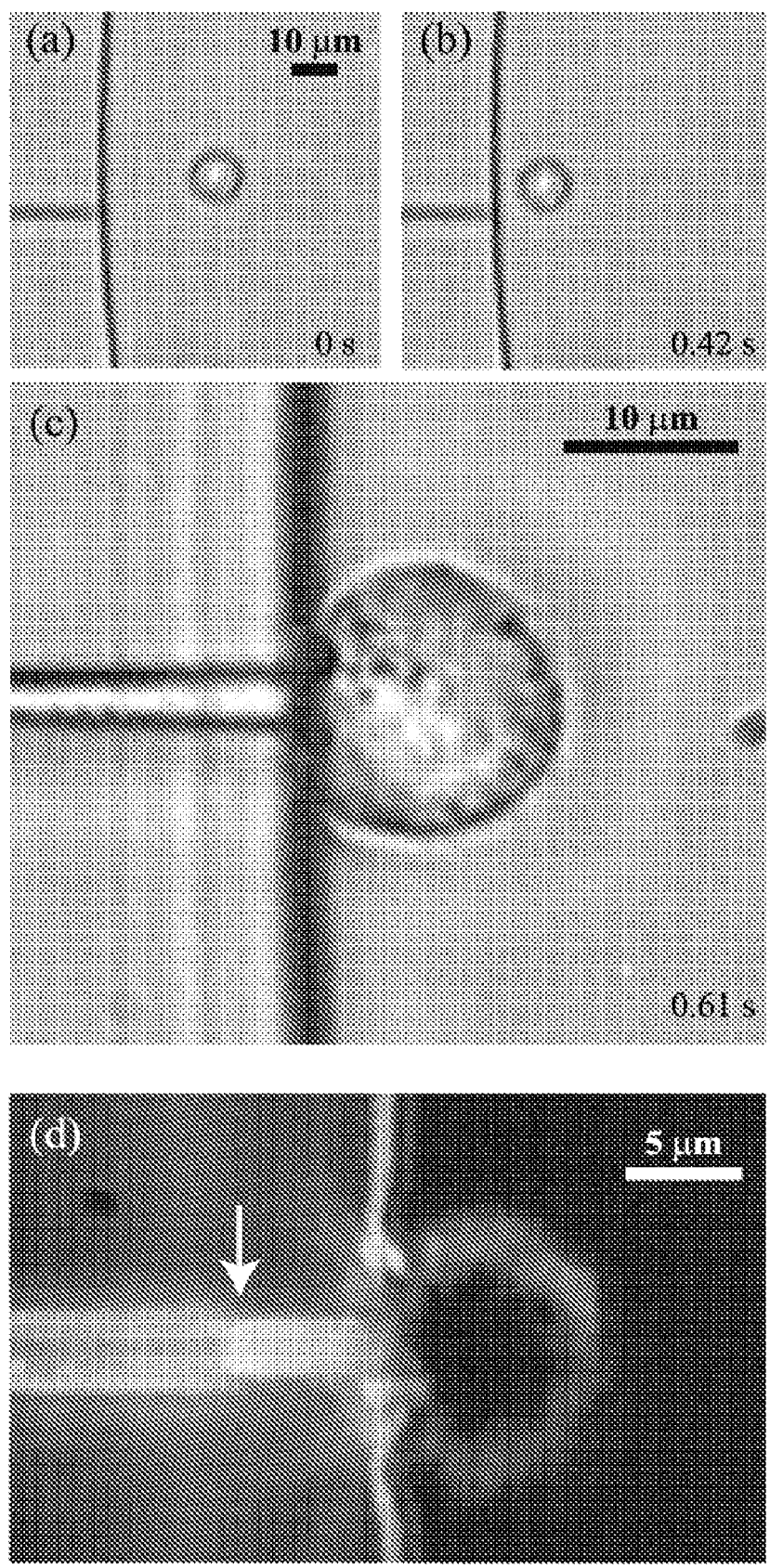
FIG. 7A-D show four frames from a micrograph movie showing a HeLa cell being trapped at a lateral junction by applying a negative pressure (e.g., 2 psi) to a trapping channel according to specific embodiments of the invention.FIG.

FIG. 7A-D show four frames from a micrograph movie showing a HeLa cell being trapped at a lateral junction by applying a negative pressure (e.g., 2 psi) to a trapping channel according to specific embodiments of the invention. In FIG. 7C, the frame is magnified in order to show cell positioning on the pore. In FIG. 7D, real time observation of the cell membrane deformation is shown. In this example figure, pore openings are approximately 1-3 microns in cross-section.

As can be seen in the example figures, fluorescent images of trapped cells indicated that the cell membrane routinely protrudes large distances (x>10 lm) into the channel for a relatively low trapping pressure of 28 kPa. Therefore, seal formation is not restricted to the recording capillary orifice, and can occur several micrometers along the length of the capillary. A pressure spike leads to a membrane break, corresponding to a rise in cellular capacitance. Cytoplasmic access can also be confirmed by observing the diffusion of dye from the cell interior into the recording capillary. The ability to make these types of measurements is a unique advantage of the lateral trapping design, because both the recording capillary and the cell are in the same optical plane. Mechanical and electrical breakdown of the membrane and dye diffusion out of the cell can be quantified, and such data can be used to characterize single cell electroporation on a similar platform.

5. Electroporation and Electrofusion Operation

In one operation example, the feasibility of electroporating single cells using an elastomeric device with small (3×4 μm) lateral trapping/electroporation channels was shown by electroporating Hela cells using low applied voltages (<1V). The average transmembrane potential required for electroporation of Hela cells is 0.51V+0.13. Membrane permeation was assessed electrically by measuring characteristic 'jumps' in current that correspond to drops in cell resistance, and microscopically by recording either the escape of a cytoplasmic dye Calcein AM or the entrance of Trypan blue stain. The device configuration focuses the electric field, eliminating the need to manipulate electrodes or glass pipettes and allows parallel single cell electroporation.

As described above, the invention hydrodynamically traps individual cells at the point of largest potential drop. This avoids the need to manually manipulate electrodes to target an immobilized cell as is common in traditional single cell electroporation set-ups. In specific embodiments, the electrodes or electrical connections can be placed far from the trapping site, an improvement over some earlier designs in which it is critical to place the electrodes as close to the cell as possible.

In specific embodiments, the invention makes use of a trapping channel whose height (e.g., about 3.1 μm) is approximately a third of the cell's diameter. A large inlet channel (e.g., cross-section: 200×50 μm) is used to introduce the cells into the device; the cells flow freely pass the trapping channels. A cell is hydrodynamically trapped by applying negative pressure to the trapping channel via an attached syringe or other suction mechanism as a cell passes by.

By sequestering individual cells in PDMS channels before electroporation, the invention focuses the electric field such that the greatest potential drop occurs across the first membrane of the cell. In this way, localized electroporation can be achieved at relatively low applied voltages.

Using one of the example chip layouts shown, a large circular chamber allows cells to move at a relatively slow speed (~20 μm/s) compared to the speed of the cells in the inlet channel (~100 μm/s). The trapping channels are arrayed around the circular chamber to sequester individual cells. The cross-sectional dimensions of an example trapping channels are 4 μm×3.1 μm.

Because resistance is inversely proportional to surface area, the small portion of the cell inside the immobilizing channel has a much higher resistance (~80×) than the portion outside the channel. The greatest potential drop therefore occurs across the portion of the cell membrane inside the channel. In this configuration, low applied voltages are sufficient to achieve electroporation with a high electric field across that first membrane (~750 kV/cm). Furthermore, the planar aspects of the invention in specific embodiments allows for parallel trapping and electroporation of several cells. This design also enables the electrodes to be placed a distance away from the cell, eliminating the potential of adverse products from reactions occuring at the electrodes.

In further embodiments, a system of the invention uses Ag/AgCl electrodes and a patch clamp amplifier, allowing accurate current traces not commonly reported in electroporation experiments. Ag/AgCl electrodes have smaller double layers and less loss of applied potential at the solution interface. Finally, the trans-parent PDMS, unlike opaque silicon, enables fluorescent detection and monitoring.

Figure 8:
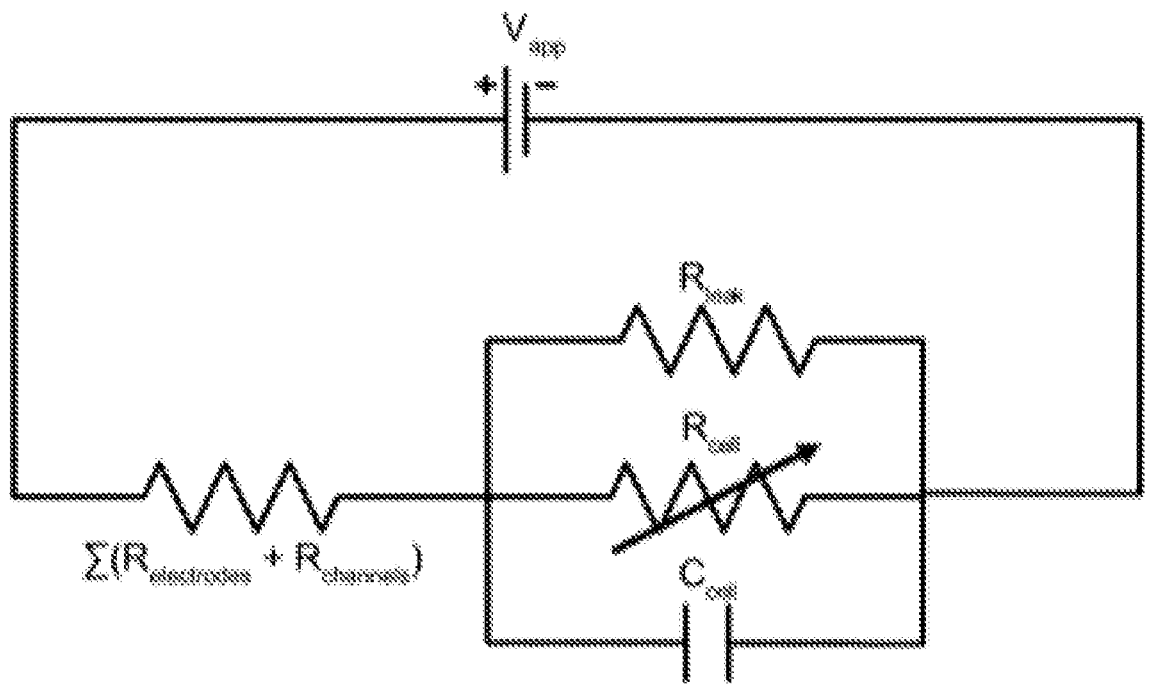
FIG. 8 illustrates aspects of an example circuit model of a cell according to specific embodiments of the invention

FIG. 8 illustrates aspects of an example circuit model of a cell according to specific embodiments of the invention The potential drop across the cell is significantly greater than any other potential drop. Therefore, other cells in close proximity to the trapped cell would not be electroporated by the electric field. The cell itself is modeled as a parallel combination of a resistive $R_{cell}$ and a capacitive $C_{cell}$ element (whose effect is transient). The $R_{leak}$ is the resistance of the pathway where the current by-passes the cell, thus it is in parallel to $R_{cell}$. $R_{leak}$ is determined from the initial current at low voltages, when $R_{cell}$ is so high such that all the current can be assumed to go through $R_{leak}$. It is assumed that $R_{leak}$ remains constant before and after electroporation. After electroporation the only element that changes in the model is the $R_{cell}$, which drops because of the formation of electropores.

Since the phospholipid membrane of the cell has much higher resistance than both the cytosol and the extracellular medium, only the potential drop across the membrane is significant. The resistance of the cell can thus be further broken down into the resistance of the membrane inside the channel ($R_{mem\_channel}$) and the resistance of the membrane outside the channel ($R_{mem\_outside}$). By approximation from trapped cell images, the membrane surface area outside of the channel is about 80 times that of the membrane within the channel. This implies that $R_{mem\_channel}$ is about 80 times larger than $R_{mem\_outside}$. Hence the resistance of the cell can be approximated as solely the resistance of the membrane within the channel. This resistance distribution gives rise to localized electroporation of the cell membrane within the channel.

In addition to recording electrical measurements, two different assay experiments were performed to verify poration: recording either the escape of Calcein AM or the entrance of Trypan blue. Calcein is membrane permeant; in live cells, the non-fluorescent Calcein AM is converted to green-fluorescent Calcein by intracellular esterases. The resulting fluorescent Calcein is highly charged and therefore cannot be excised from the cytoplasm once it has infiltrated the cell unless non-selective electropores are introduced. The high sensitivity Calcein AM fluorescence is useful in quantifying the diffusion of dye out of the cell once the cell is electropermeated. The color of the membrane impermeant dye Trypan blue is normally undetectable at low concentrations; once the membrane is permeabilized and the dye can accumulate within the cell, a dark blue color becomes apparent. Therefore, by using the Trypan blue assay, the electro-permeated area can be readily visualized.

Thus, according to specific embodiments, devices and systems as described herein can selectively immobilize and locally and reversibly electroporate single cells with less than 1 V. Moreover, the electroporated cell can be simultaneously monitored electrically (via impedance measurements) and optically (via fluorescence detection), enabling multiplexing for high content screening. An improved electroporation device of the invention provides more controlled intracellular compound delivery by either: (1) using intracellular perfusion and (2) using preloaded vesicles or cells to deliver compounds to the targeted cell via electrofusion.

Example Experimental Set-up

In an example set-up, Ag/AgCl electrodes are connected via tubing to one of the main channels of the chip, and to one or more of the immobilizing channels. These electrodes, which serve both to apply the voltage and record the current, are good recording electrodes because of their minimal electrical double layer (EDL). The other main channel is connected to a syringe for cell loading. The two electrodes are connected to an amplifier (PC-ONE Patch clamp, Dagan) which provides the voltage and measures the current. The amplifier is controlled by a custom-made Labview (National Instruments) application through a data acquisition card (PCI-6024E, National Instruments). The chip is monitored with an inverted microscope (Eclipse TS100, Nikon) with a fluorescent module and is video captured with a camera (DXC-190, Sony) and a video capture card (microVideo DC50, Pinnacle) on the same computer.

Figure 9A:
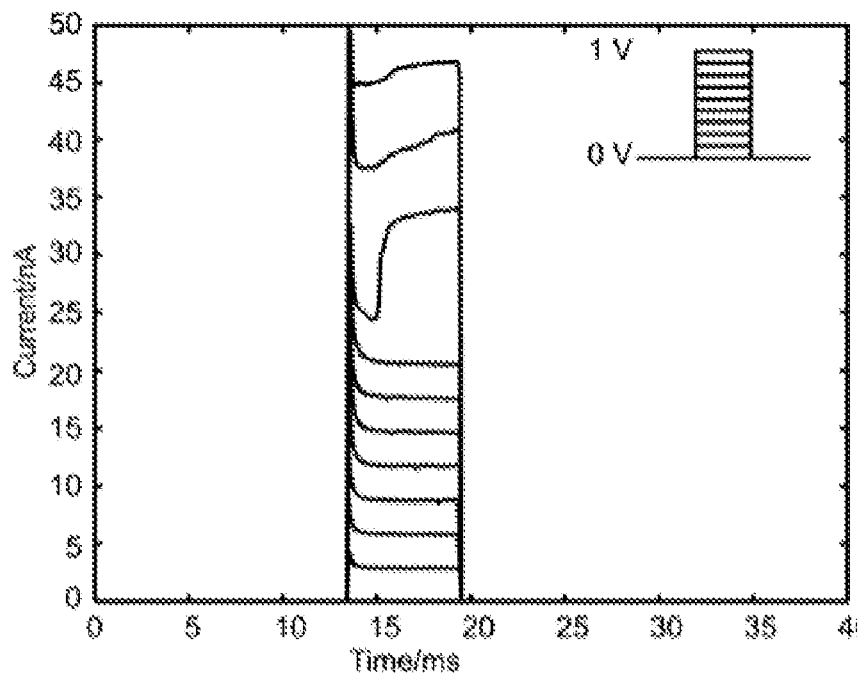
FIG. 9A-B are graphs illustrating example electrical measurements according to specific embodiments of the invention where (A) Short square wave voltages (inset) are applied to the circuit and the resulting current is measured; and (B): The leak current $R_{leak}$ is linear and subtracted from the measured current to isolate the current across the cell, $R_{cell}$.

To start the electroporation experiments, all channels in the chip are filled with filtered PBS solution and extra care is taken to expel any air bubbles in the tubing. The linear resistance of the open channel is first measured via the amplifier to be ~12 M_. The cell/dye suspension is then introduced into the device after incubation with a syringe; the injection is controlled manually to allow cell trapping by applying negative pressure on the trapping channel. Once a cell is trapped, a 'current-voltage trace' program written in Labview is run to input a sequence of pulses with increasing amplitude (at 0.1V intervals from 0V to 1.0V) while recording the current at a sampling rate of 10 kHz (FIG. 9A, inset). A second sequence of pulses is also applied 60 s after the first sequence to allow time for resealing.

Figure 9B:
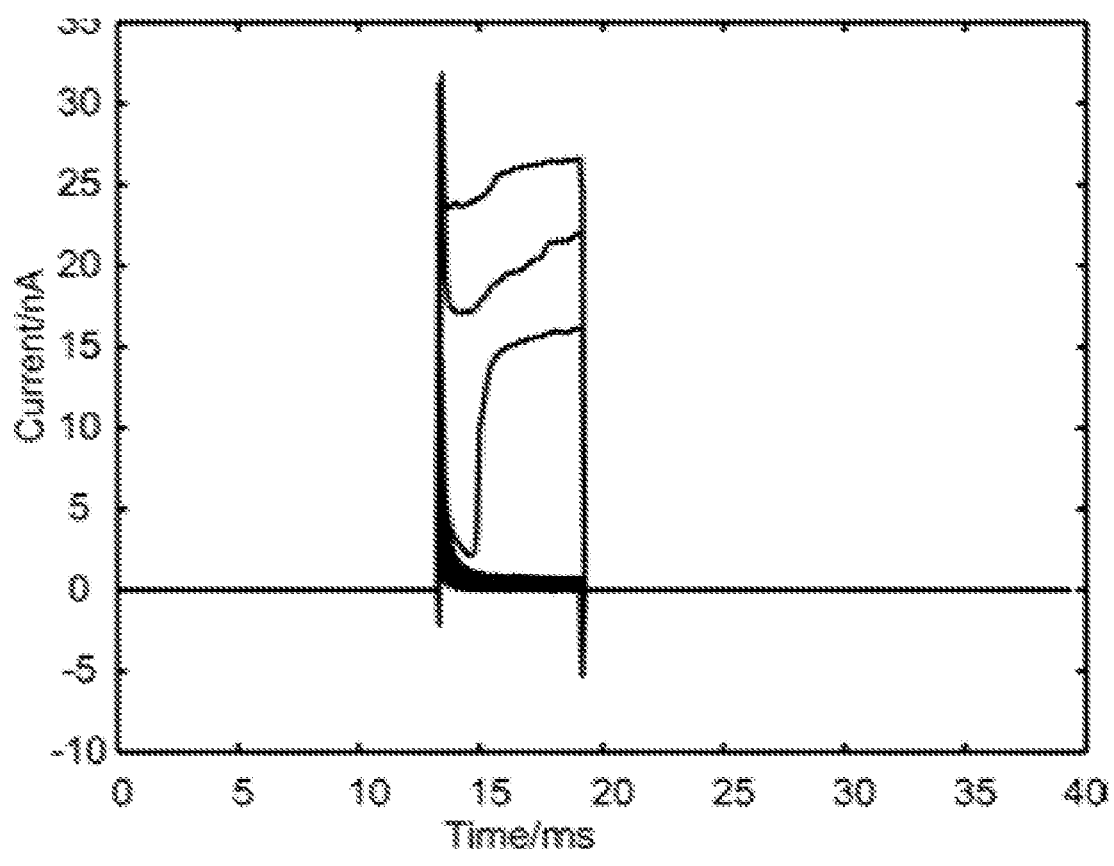

With the pulse duration at about ~6.5 ms, recording was performed from 17 Hela cells. The characteristic 'jump' in current is observed in 15 of the 17 cells. The volt-age is varied from 0 to 1V in 0.1V intervals. A typical resulting current trace from one of the cells is shown in FIG. 9A. Leak current, i.e. the cur-rent that goes around the cell because the seal resistance is not infinite, is subtracted (based on the circuit diagram depicted in FIG. 8) to isolate the current across the cell (FIG. 9B). The leak resistance, $R_{leak}$, is measured for each cell from initial current traces at low voltages and assumed to be constant (~35M_). A significant jump in current is evident at 0.8V. The average applied voltage of electroporation for the 15 cells that show jumps is 0.76V+0.095. As discussed before, the major potential drop is across the membrane trapped in the channel. Hence, for this cell, the transmembrane voltage across the electroporated membrane is ~0.6V, which is within the voltage range (0.2-1.5V) of dielectric breakdown suggested by most published data [3,4]. The average transmembrane potential for the popluation of cells is 0.51V+0.13.

Figure 10:
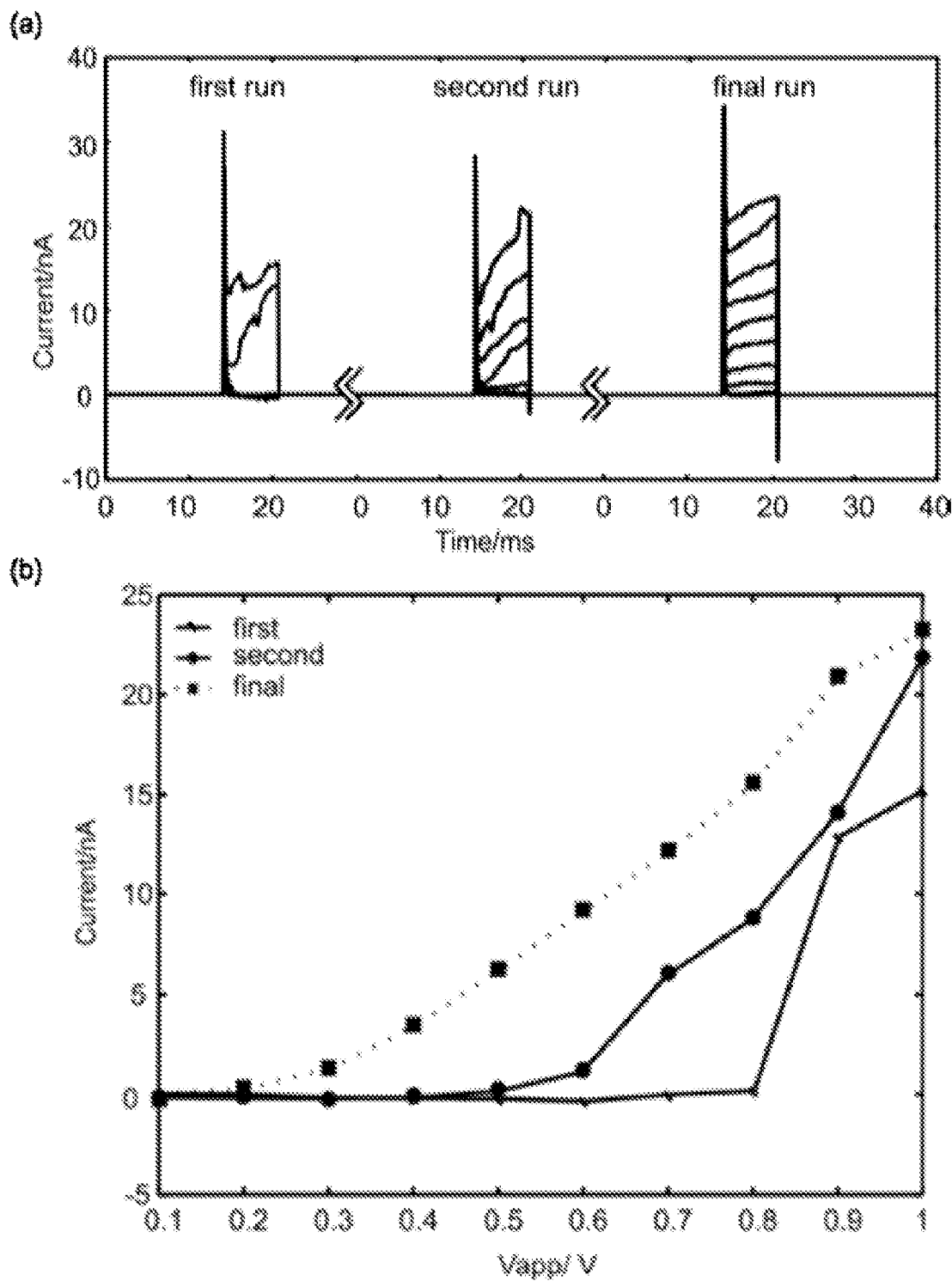
FIG. 10A-B are graphs each illustrating example electrical measurements for three different runs demonstrating reversible electroporation according to specific embodiments of the invention.

The data also demonstrates evidence for cell resealing. FIG. 10A-B are graphs each illustrating example electrical measurements for three different runs demonstrating reversible electroporation according to specific embodiments of the invention. FIG. 10A illustrates current for three consecutive pulse sequences, showing that the current in the second run pulse sequence shows similar characteristics of low current at low applied voltages as in the first run, indicating that the cell cell has returned to higher resistance and the electroporation openings have resealed. The final run data shows a cell after multiple pulse sequences, in which a much more linear response results, apparently illustrating that the cell finally loses its ability to reseal after multiple runs. Thus, after the first sequence of pulses is applied, the membrane is permeated as the current jumps to a relatively high level. However, when the second sequence of pulses is applied after 60 seconds, small applied voltages (<0.6 V) again result in very low currents, similar to those of the first sequence of pulses. This is evidence that the pores shrink after release from the electric field. In the subsequent run, the current jump occurs sooner than in the first run because the pores still exist; therefore, it is easier to reopoen them with the electric field than to create new ones. The final run in the sequence is presented to compare the resealing capabilities with the more linear response of a cell that has lost its ability to reseal.

Figure 11:
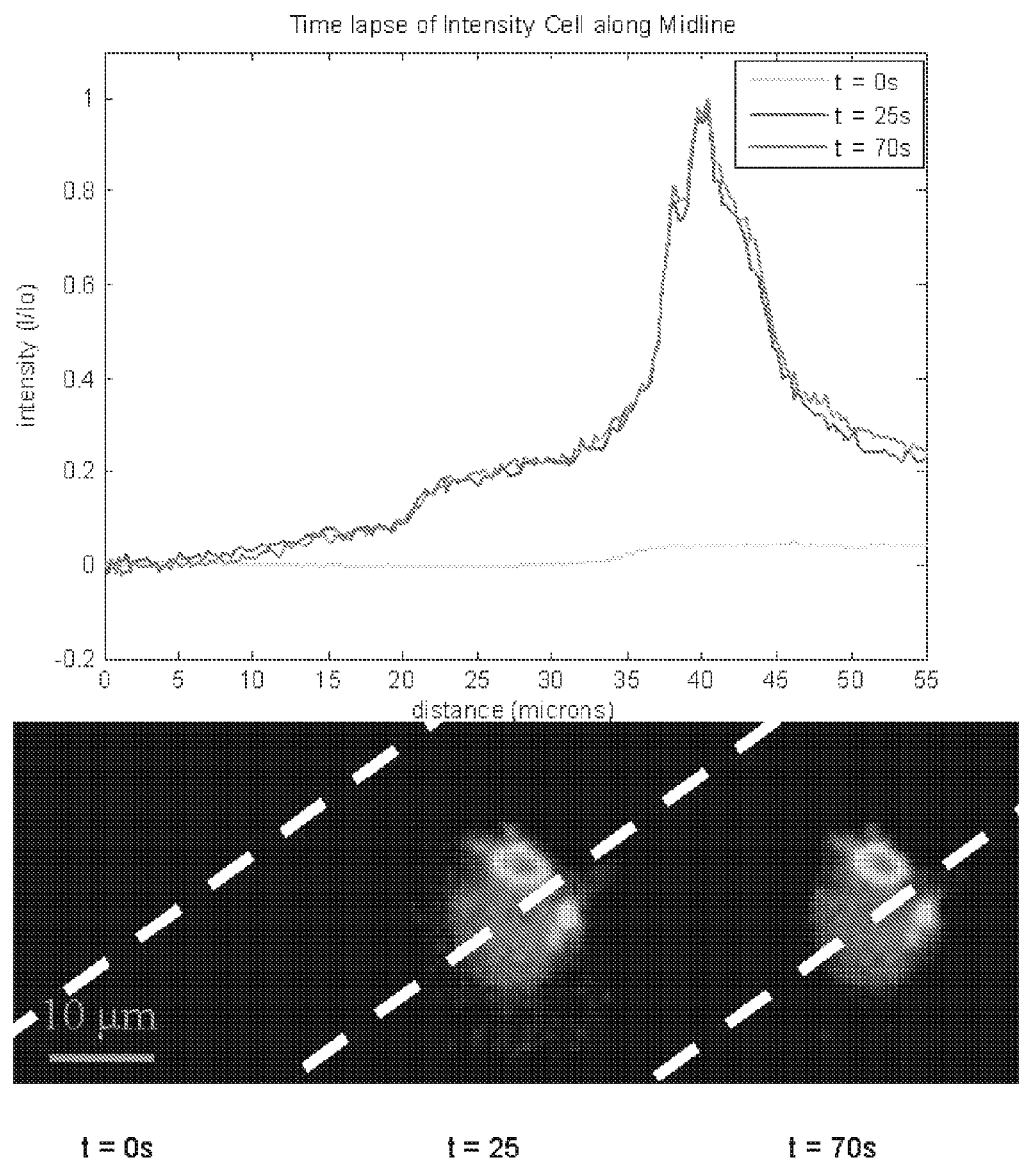
FIG. 11A-B illustrate electrical and optical characteristics of a Hela (human carcinoma) cell electroporated and loaded with propidium iodide from the intracellular perfusion channel (e.g., as described above) according to specific embodiments of the invention.
Figure 15:
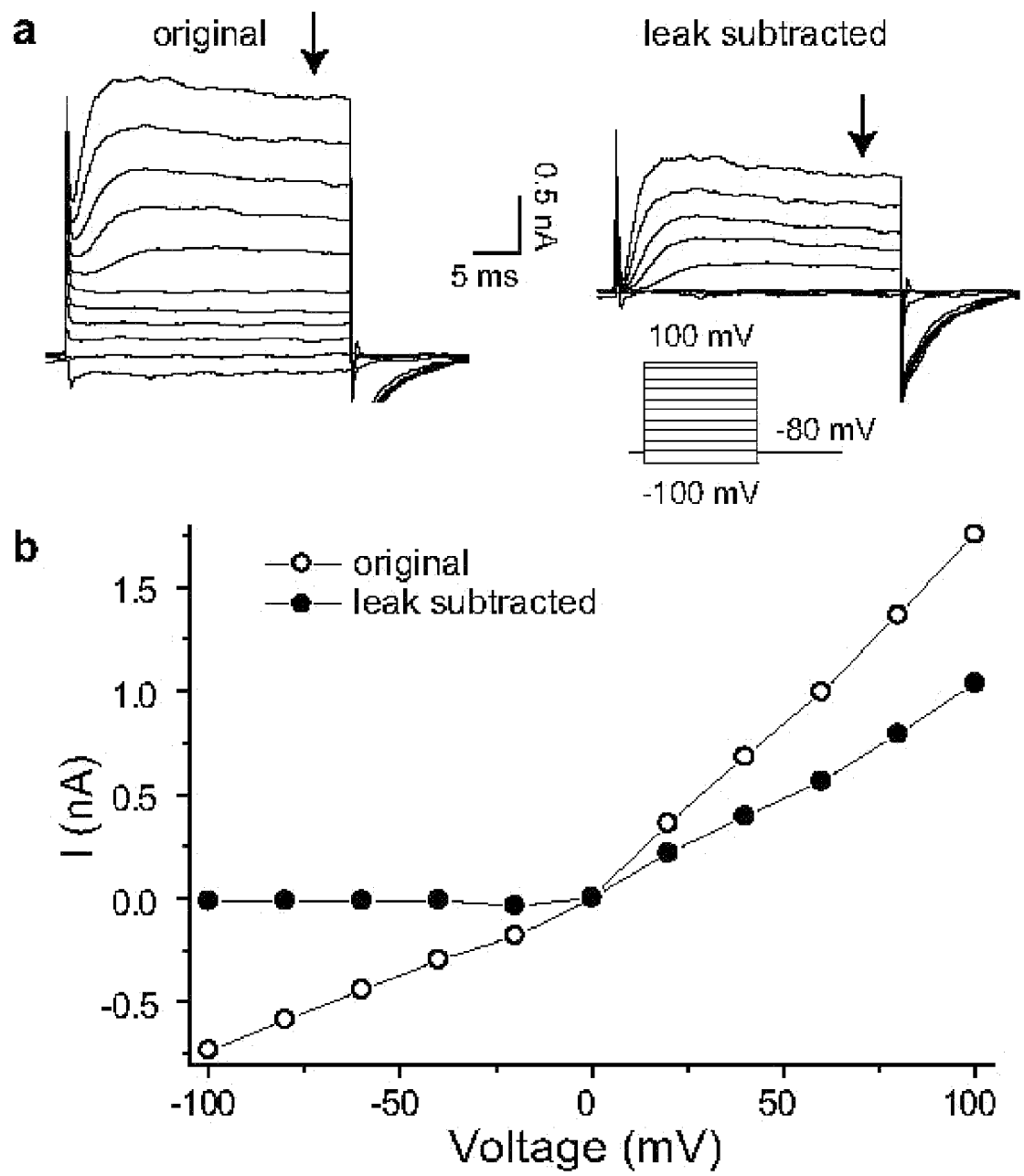
FIG. 15 is a diagram showing an example of whole mammalian cell currents recorded according to specific embodiments of the invention.

FIG. 11A-B illustrate electrical and optical characteristics of a Hela (human carcinoma) cell electroporated and loaded with propidium iodide from the intracellular perfusion channel (e.g., as described above) according to specific embodiments of the invention. Valves at each end of the perfusion channel allow compounds to be introduced after a cell is trapped. FIG. 11A shows typical current versus time graph wherein a jump in current correlates with electroporation and a decrease in electrical resistance because of the pores. FIG. 11B illustrates optical measurements of intracellular perfusion. Cell is trapped, electroporated, and loaded with propidium iodide from the backside. The graph is the time lapse intensity of the cell's cross section.

FIG. 12A-B are micrographs illustrating electrofusion of two cells (A) and two vesicles (B) according to specific embodiments of the invention. FIG. 12A shows two Hela cells (membranes dyed with rhodamine) trapped in the cell fusion device after the electric field has been applied. FIG. 12B shows two vesicles trapped. For an example electrofusion operation, 3V for 30 ms was applied across the cells. Unlike the PBS used for electroporation, the electrofusion media was a combination of BSA with glucose and magnesium and chloride ions. Furthermore, the time required for electrofusion was significantly longer (~20 minutes). The membrane of the two cells stuck together and transfer of calcein was observed. Other pulse parameters and medium for electrofusion may be optimized in different embodiments. To demonstrate electrofusion, one Hela cell was preloaded with calcein and the other was not. After pulse application, the calcein slowly leaked into the other cell.

Thus, the invention can selectively trap targeted cells and focus the electric field for reversible electroporation (in which the pores reseal), intracellular perfusion, and cell fusion while simultaneously monitoring the cell electrically and optically.

In further embodiments, lateral trapping junctions of the invention can be embodiment into larger-scale integrated systems for high-throughput cellular analysis and previously described.

Figure 19:
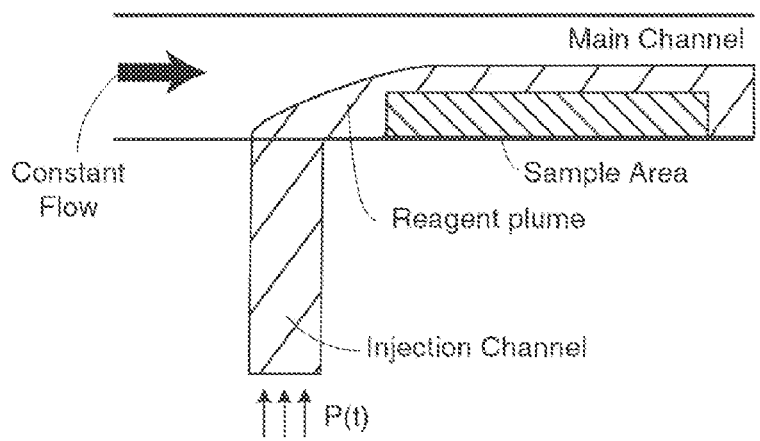
FIG. 19 is a schematic representation of a basic design unit for fast reagent application and removal according to specific embodiments of the invention.

A basic example operation unit of this approach comprises a main channel (containing the reaction target) and an injection channel (used for reagent delivery). A schematic is shown in FIG. 19. In operation, a generally constant flow is supplied to the main channel (e.g., via a syringe pump) and the injection channel is being driven by a pressure (or flow) source at the channel inlet P(t)—pressure as a function of time. When P(t)>P0 (Po=the pressure in the main channel), a plume of solution form in the main channel, engulfing the sample area. If P(t)<Po, no reagent enters the main channel, and the existing plume is removed quickly by the existing flow velocity in the main channel. While the configuration of channels can be varied according to specific embodiments of the invention, one desirable configuration is a lateral configuration where all the channels are in roughly horizontal planes. Thus, this and subsequent related figures can preferable be viewed as top-down view or bottom-up view of a device, with lateral channels therein.

Figure 20:
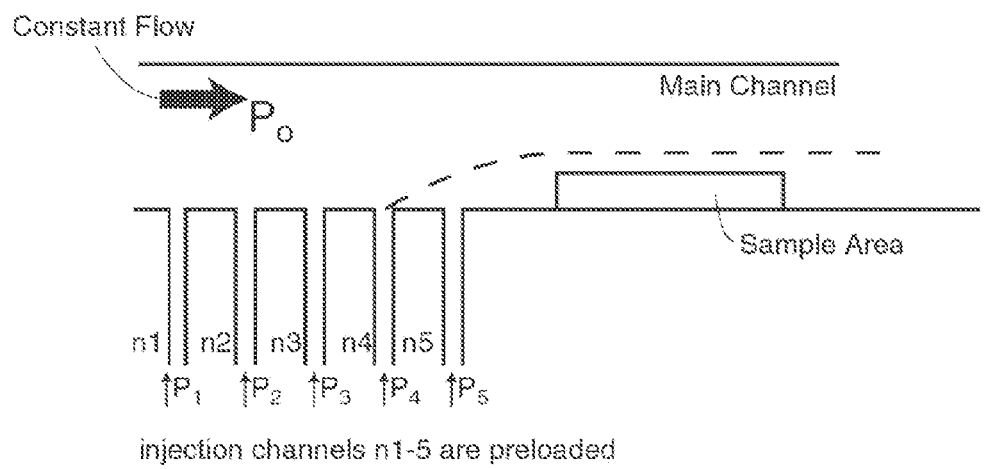
FIG. 20 is a schematic representation showing an example methodology for the application of multiple reagents to a target sample area according to specific embodiments of the invention. (A state where channel n4 is on is shown).
Figure 21:
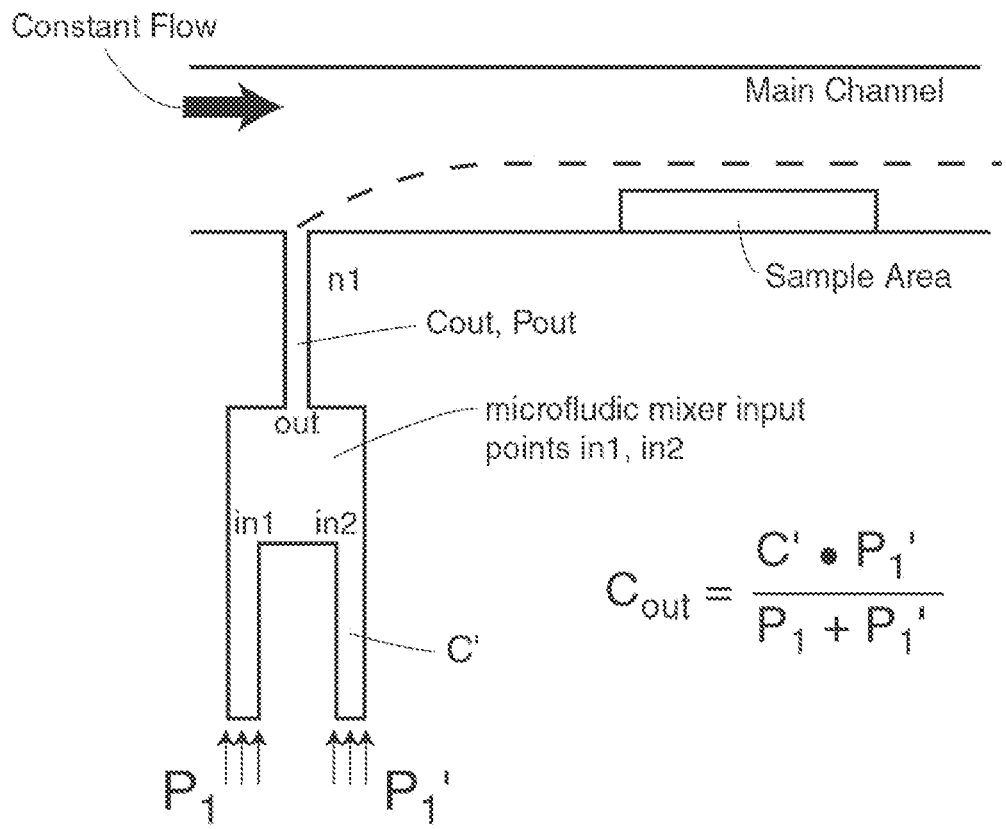
FIG. 21 is a schematic representation showing an example methodology for applying an arbitrary concentration to a sample area according to specific embodiments of the invention. (A microfluidic mixer is being driven by input pressures/flow rates in this example.)
Figure 22:
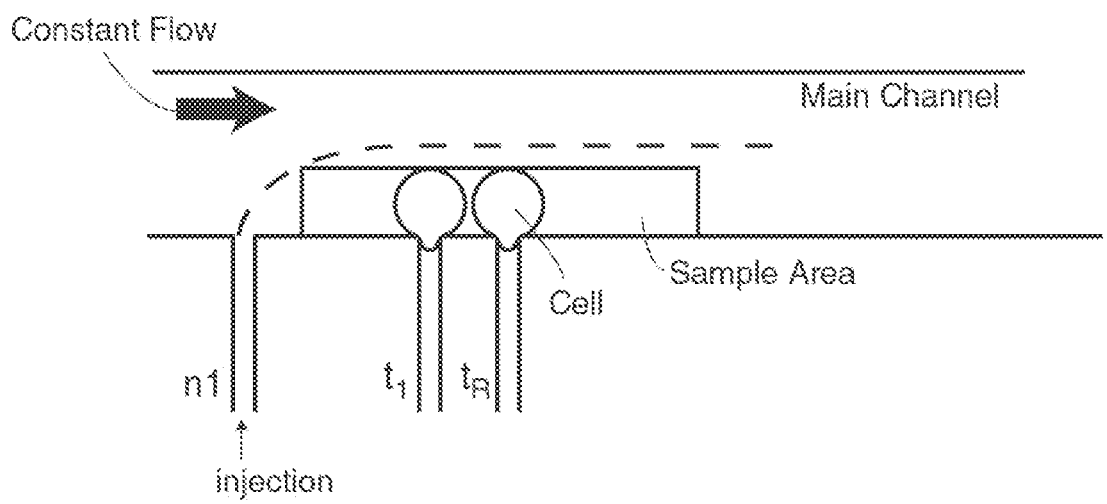
FIG. 22 is a schematic representation showing use of trapping channels for immobilizing cells in the target area for fast reagent application and removal according to specific embodiments of the invention.

In specific embodiments, because flow in the main channel follows laminar profiles, the distance between the injection channel and the target sample area is not a critical parameter. Therefore, multiple reagents can be applied by simply arraying a number of injection channels. In FIG. 20, injection channels n1-5 are preloaded with relevant reagents and controlled individually by input pressures Pi-s(t). The pressure application can be timed so that only one channel is on at a time, or multiple channels are on simultaneously. In FIG. 20, a situation in which channel n4 is on is displayed. This can be achieved for example by setting Pi-3<Po, Ps<Po, and P-4>P0 so that a plume is only present at the outlet of channel 4.

6. Example Fabrication

Systems and devices as described herein can be fabricated using any techniques or methods familiar from the field of photolithography, nano-fabrication, or micro-fluidic fabrication. For completeness of this disclosure and to discuss additional and independent novel aspects according to specific embodiments of the invention, specifics of example fabrication methods are provided below.

Example fabrication steps according to specific embodiments of the invention are shown diagrammatically in FIG. 13(a-f). In this example, a silicon or other suitable substrate mold is prepared using surface micromachining and/or photolithography techniques. In other examples, any other appropriate material and any other techniques for making a mold could be used.

In a micromachining example according to specific embodiments of the invention, first, 3.1 μm height patterns are made, defining the narrow cell trapping channels using deep reactive ion etching (FIG. 13A). Second, 50 μm high patterns are added for wide connection regions using SU-8 negative photoresist (FIG. 13B). After a base and a curing agent of PDMS were mixed (1:10), the liquid mixture is poured onto the mold and cured at 80° C. for 1 hour (FIG. 13C).

After the PDMS is cured, the devices are detached and can be mechanically punched. In this specific example, the devices and the glass substrate pre-coated with a thin PDMS layer are treated with oxygen plasma (FIGS. 13D and E) and the devices are bonded to the thin PDMS (FIG. 13F).

SEM images of overall device geometry before bonding (upside down) and a closeup of the patch pore after bonding are shown in FIGS. 13G and H. A SEM image of the mold is shown in FIG. 13I.

In this example, it was observed that the top of the orifice is rounded. The rounding of the top of the orifice is a beneficial result of mold fabrication, and it was observed that the channel top is rounded next to the patch orifice in the mold (FIG. 13I). When the SU8 is selectively polymerized in order to create the large channels on top of the small patch channel defined in Si, light scattering near the Si surface results in a deviation from the intended vertical SU8 wall. The resulting rounded feature at the bottom of the SU8 wall (FIG. 13I, arrow A) is also present on top of the small Si wall (FIG. 13I, arrow B), resulting in rounding of the patch orifice top. This feature is reproducible in specific fabrication embodiments at every patch orifice.

For fluidic connections to outside tubing, 0.5 mm holes can be punched mechanically into the cured and detached PDMS device. The device can be subsequently bonded to a thin PDMS layer which is spin cast and cured onto a glass substrate. Plastic or other tubes can be connected to the reservoirs, via punched holes, to load both cells and electrolyte solutions and to apply suction to the patch channel.

Example Alternative Fabrication Methods

The following further example fabrication methods are provided for completeness of this disclosure. It will be recognized from these teachings that many alterations can be made to this method to accommodate different materials and/or methods of manufacturing and/or to provide different configurations as otherwise described herein.

A specific example device according to embodiments of the invention can be fabricated as follows, similarly as described above. First, a mold is prepared using surface micromachining techniques. As an example, first the narrow patch capillaries are made with 3.1 micron high patterns using deep reactive ion etching. Recording capillaries are 20 microns apart, which allows trapping of, for example, 12 cells along a main channel in a volume of 0.36 nL (150×60×40 micron$^3$ for length, width, and height, respectively). Therefore, in the active device area, the reagent dead volume is 30 pL per recording site. Second, 50 micron high patterns are added for wide connection regions, for example using negative photoresist. After the PDMS (e.g., Dow-Corning Sylgard 184) base and curing agent were mixed (at an example ration of 1:10), the liquid mixture is poured onto the mold and cured at room temperature for 24 hours. For fluidic connections to outside tubing, 0.5 mm holes were punched mechanically into the cured and detached PDMS device. A thin PDMS layer was spin cast on a glass substrate at 3000 rpm for 30 seconds and partially cured (e.g., 90° C. for 1 min.). The device is bonded to the substrate by gently placing the two in contact and fully curing the bottom layer (120° C. for 5 minutes). For use, plastic tubes are connected to the reservoirs, via punched holes, to load both cells and electrolyte solutions and to apply suction to the channel.

Partial cure bonding improves the geometry of the recording capillary by altering the final geometry of the bonded and cured capillary allowing for a tight seal between the cell membrane and the capillary walls even with the hydrophobicity of the PDMS. Partial curing is believed to affect the cross-section of the trapping channel geometry, where instead of providing a square cross-section provides a rounded cross section allowing for a more stable seal.

7. Example Operation

FIG. 14A-B illustrate current response to a 20 mV voltage pulse before (a) and after (b) cell trapping of an example device according to specific embodiments of the invention. Disassociated cells were suspended in PBS and injected into the main channel. Gentle pressure (1 psi) was applied to the trapping connection while cells were loaded into the main fluidic channel in order to prevent contamination at the trap site. A cell can either be trapped randomly or selectively by controlling the flow through the main fluidic channel. In specific example experiments with an early design, it was found that a cell within 100-200 μm of the channel opening can be trapped within a 1 s time interval by applying 2 psi of negative pressure to the channel.

Right after trapping the cell, negative pressure was removed and the cell was allowed to form a seal with the rim of the channel. In specific embodiments, membrane protrusion into the channel can be seen using standard microscopy and visualization of trapping can be used to control pressure application. In alternative embodiments, cell trapping can be confirmed for example by measuring the resistance at a pore and using the change in measured resistance to confirm the presence of cell and to reduce pressure at that pore where desired.

The current response from the cell by a 20 mV/50 ms current pulse is shown in FIG. 14B. By applying positive pressure to the trapping channel, the trapped cell was expelled from the channel. As soon as the cell was expelled, the current response returned to that of the open channel. Subsequent cell trapping in the same channel resulted in lower seal resistance, presumably due to contamination at the opening of the trapping channel. In specific embodiments, the invention proposes a single use cell-trapping device, so this contamination does not affect overall usability. In alternative embodiments, a variety of known cleaning techniques could be used to remove contamination from the cell pores.

In experimental results such as with the device illustrated in FIG. 6, electrical connection to the recording capillaries is achieved by inserting Ag/AgCl electrodes into tubing connections outside the active area of the device. The electrodes are in turn connected to the inputs of a multiplexer circuit, which connects to electric signal generates for electroporation and/or electrofusion and may also feed into a headstage of a traditional patch clamp amplifier (in an example system, a customized multiplexor was used in combination with PC-ONE patch clamp components from Dagan, Minn.). The amplifier was driven by custom software (for example, written in a LabView programming environment) and interfaced via an analog to digital conversion board.

Once the device is filled, adherent cells are trypsinized, spun down at 1000 rpm for 5 minutes, and resuspended in sterile electrolyte solution at a concentration $5 \times 10^6$ cells/ml. A 3 ml syringe is used to inject cells into the main channel. Gentle positive pressure (7 kPa) is applied to the patch channel while cells were loaded into the main fluidic channel in order to prevent contamination at the patch site. A cell can either be trapped randomly or selectively by controlling the flow through the main fluidic channel. A cell found within 100-200 microns of the patch channel opening could be trapped within a 3 s time interval by applying 14-21 kPa of negative pressure to the patch channel. Immediately after trapping the cell, the negative pressure is removed and the cell is allowed to form an electrical seal with the patch channel orifice. Patch array measurements can be performed without the use of vibration isolation equipment.

For patch analysis and traditional electrophysiology, currents were sampled at 5 kHz and filtered with a 2 kHz low-pass Bessel filter. The holding potential was −80 mV and depolarizing stimuli were applied at an interval of 10 s, unless otherwise specified. All signals were post-processed with automated leak subtraction by custom written routines that subtracted a calculated leak current (square wave) from all data traces. The leak resistance was assumed to be constant, and obtained by dividing the resting potential (−80 mV) by the current passed at that voltage.

Both internal and external electrolyte solution contained (mM): 140 KCl, 2 $CaCl_2$, 2 $MgCl_2$, 20 HEPES, 10 Glucose. pH was adjusted to 7.3 with KOH and osmolality adjusted to 300 mOsms with glucose.

Thus, in specific embodiments, the invention can be embodied as a disposable electromanipulation microarray with integrated microfluidics as an electrophysiological tool. Key features of specific example designs include high electroporation site density, built-in integration with microfluidics, and the ability to study cells by standard microscopy techniques during handling. A micromolded array according to specific embodiments of the invention is capable of mammalian cell recording in a high density format. The device contains an array of lateral capillaries which trap cells efficiently to form tight electrical seals. This scheme has the advantage of integrated microfluidics for compound exchange on both the intracellular and extracellular sides of the cell membrane. The distance between trap sites can be on the order of 20 μm.

Another convenient feature of this design is the low fluidic volumes associated with perfusion chambers and channels. In one example design, the volume of the main chamber containing 12 cell holding sites is 0.36 nL. By comparison, other planar technology can require reagent volumes of 10-100 microL per site. Therefore, the reduction in dead volume over such proposals is of order $10^4$. This allows rapid solution exchange to expose attached cells to different reagents in fast succession, with very small reagent consumption and highly uniform solution content between the arrayed sites.

8. Array of Hollow Cylindrical Electrodes for Microfluidic and Electric Interface According to further specific embodiments of the invention, an arrangement of hollow Ag/AgCl cylindrical electrodes can be used with a microfluidic electroporation system as described above to serve as both a fluidic interface and an electrical interface for microfluidic chips. In specific embodiments, as fluid flows through these hollow electrodes, electrical and fluidic connections are established. This eliminates the need for fragile, cumbersome, and expensive Ag/AgCl pellet electrodes that have often been used in patch clamp applications and also minimizes microfluidic circuitry. While polymeric devices themselves can be manufactured for just pennies a piece, the high cost of the electrodes can be a the cost-limiting factor. Additionally, the delicate pellet electrodes tend to break easily, especially because they are jammed into the fluidic tubing while the fluid must flow around them.

While electrodes made of noble metals can be easily deposited onto a glass substrate, Ag/AgCl is more difficult. Integrated thin film Ag/AgCl electrodes have been demonstrated but have their drawbacks. In further specific embodiments of the invention, low cost electrodes are provided that can efficiently mate with various microfluidic systems, including systems described herein. Such electrodes are critical, for example, to electro-physiological manipulations and measurements for high through-put screening. The invention, therefore, according to specific embodiments, routes fluid flow through instead of around the electrodes using a detachable Ag/AgCl array, for example built on a printed circuit board (PCB). These electrodes, according to specific embodiments of the invention, serve not only as electrical connections, but fluidic conduits as well.

In specific examples, fluid flows through the hollow Ag/AgCl electrodes that connect the device to tubing that then connects to a syringe for sample loading. The configuration of the electrodes, as well as additional processing capabilities, can be specifically designed to mate with the microfluidic device.

Figure 16:
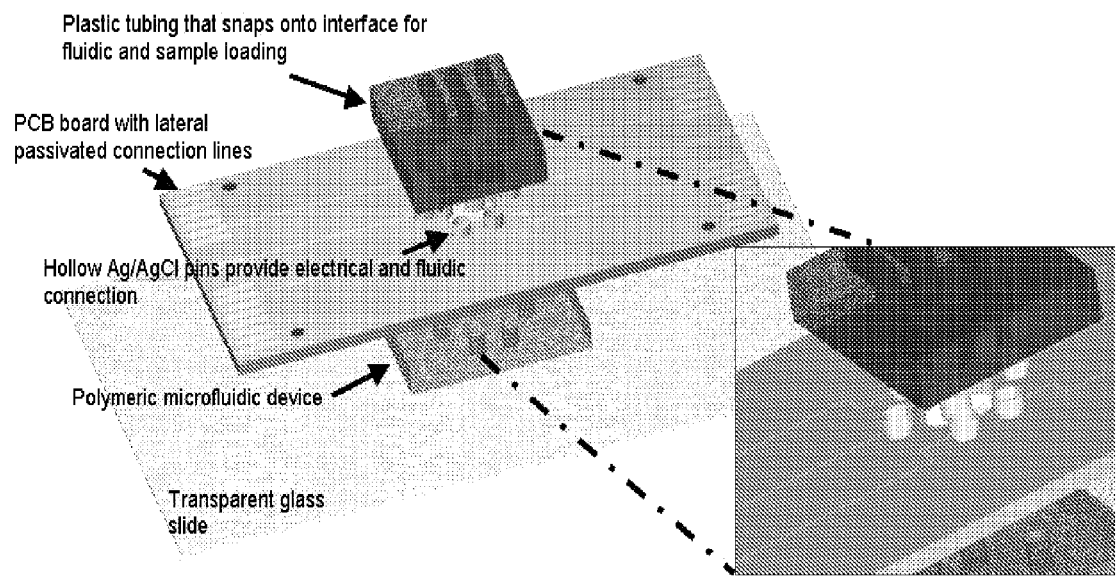
FIG. 16 illustrates an example schematic of a hollow electrode interface (in this example configured on a PCB) mating with device and tubing according to specific embodiments of the invention.

FIG. 16 illustrates an example schematic of a hollow electrode interface (in this example configured on a PCB) mating with device and tubing according to specific embodiments of the invention. In this figure, the conduit/electrodes are embedded in a detachable PCB interface that includes passivated lateral connectors for easy electrical connection to other equipment, as will be understood in the art. In these example figures, a circular arrangement of six electrode/conduits are shown, which are arranged to mate with channel connections on a microfluidic devices and optionally also with an external source of fluidics. This is only an example arrangement, however, and any other convenient arrangement is possible.

9. Diagnostic and Drug Development Uses

As described above, following identification and validation of a assay for a particular cellular process, in specific embodiments devices and/or systems as described herein are used in clinical or research settings, such as to screen possible active compounds, predicatively categorize subjects into disease-relevant classes, text toxicity of substances, etc. Devices according to the methods the invention can be utilized for a variety of purposes by researchers, physicians, healthcare workers, hospitals, laboratories, patients, companies and other institutions. For example, the devices can be applied to: diagnose disease; assess severity of disease; predict future occurrence of disease; predict future complications of disease; determine disease prognosis; evaluate the patient's risk; assess response to current drug therapy; assess response to current non-pharmacologic therapy; determine the most appropriate medication or treatment for the patient; and determine most appropriate additional diagnostic testing for the patient, among other clinically and epidemiologically relevant applications. Essentially any disease, condition, or status for which a cellular characteristic measurable using cell electroporation can be evaluated.

Kits

A device according to specific embodiments of the present invention is optionally provided to a user as a kit. Typically, a kit of the invention contains one or more cellular electroporation devices constructed according to the methods described herein. Most often, the kit contains a device packaged in a suitable container. The kit typically further comprises, one or more additional reagents, e.g., substrates, tubes and/or other accessories, reagents for collecting blood samples, buffers, e.g., erythrocyte lysis buffer, leukocyte lysis buffer, hybridization chambers, cover slips, etc., as well as a software package, e.g., including the statistical methods of the invention, e.g., as described above, and a password and/or account number for accessing the compiled database. The kit optionally further comprises an instruction set or user manual detailing preferred methods of using the kit components for sensing a substance of interest.

When used according to the instructions, the kit enables the user to identify disease specific cellular processes and/or to introduce substances into a cell using electroporation. The kit can also allow the user to access a central database server that receives and provides expression information to the user. Such information facilitates the discovery of additional diagnostic characteristics by the user. Additionally, or alternatively, the kit allows the user, e.g., a health care practitioner, clinical laboratory, or researcher, to determine the probability that an individual belongs to a clinically relevant class of subjects (diagnostic or otherwise). In HTS, a kit according to specific embodiments of the invention can allow a drug developer or clinician to determine cellular responses to one or more treatments or reagents, either for diagnostic or therapeutic purposes.

Embodiment in a Programmed Information Appliance

The invention may be embodied in whole or in part within the circuitry of an application specific integrated circuit (ASIC) or a programmable logic device (PLD). In such a case, the invention may be embodied in a computer understandable descriptor language, which may be used to create an ASIC, or PLD that operates as herein described.

Integrated Systems

Integrated systems for the collection and analysis of cellular and other data as well as for the compilation, storage and access of the databases of the invention, typically include a digital computer with software including an instruction set for sequence searching and/or analysis, and, optionally, one or more of high-throughput sample control software, image analysis software, collected data interpretation software, a robotic control armature for transferring solutions from a source to a destination (such as a detection device) operably linked to the digital computer, an input device (e.g., a computer keyboard) for entering subject data to the digital computer, or to control analysis operations or high throughput sample transfer by the robotic control armature. Optionally, the integrated system further comprises an electronic signal generator and detection scanner for probing a patch clamp device. The scanner can interface with analysis software to provide a measurement of the presence or intensity of the hybridized and/or bound suspected ligand such as by measurement of electrical characteristics of the cell membrane.

Readily available computational hardware resources using standard operating systems can be employed and modified according to the teachings provided herein, e.g., a PC (Intel x86 or Pentium chip-compatible DOS,™ OS2,™ WIDOWS,™ WIDOWS NT,™ WINDOWS95,™ WINDOWS98,™ LINUX, or even Macintosh, Sun or PCs will suffice) for use in the integrated systems of the invention. Current art in software technology is adequate to allow implementation of the methods taught herein on a computer system. Thus, in specific embodiments, the present invention can comprise a set of logic instructions (either software, or hardware encoded instructions) for performing one or more of the methods as taught herein. For example, software for providing the data and/or statistical analysis can be constructed by one of skill using a standard programming language such as Visual Basic, Fortran, Basic, Java, or the like. Such software can also be constructed utilizing a variety of statistical programming languages, toolkits, or libraries.

Figure 17:
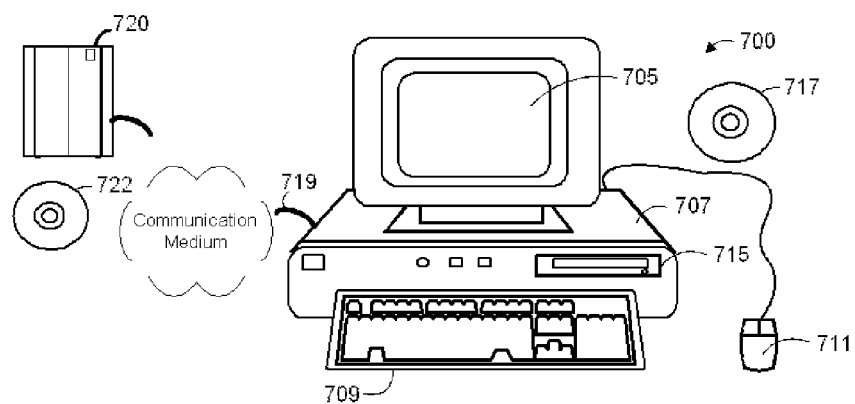
FIG. 17 is a block diagram showing a representative example logic device in which various aspects of the present invention may be embodied.
Figure 11:
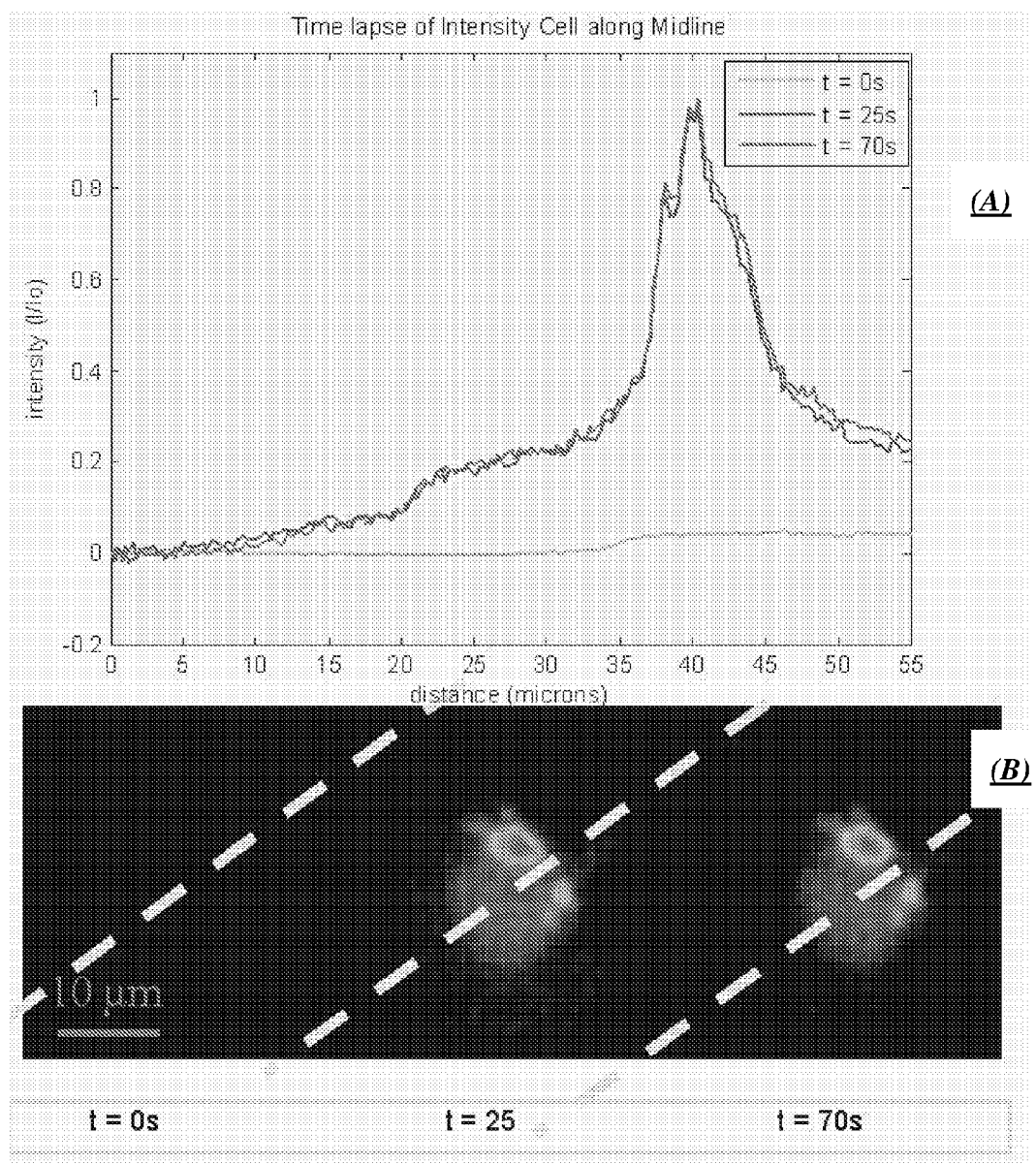

FIG. 17 is a block diagram showing a representative example logic device in which various aspects of the present invention may be embodied. FIG. 17 shows an information appliance (or digital device) 700 that may be understood as a logical apparatus that can read instructions from media 717 and/or network port 719, which can optionally be connected to server 720 having fixed media 722. Apparatus 700 can thereafter use those instructions to direct server or client logic, as understood in the art, to embody aspects of the invention. One type of logical apparatus that may embody the invention is a computer system as illustrated in 700, containing CPU 707, optional input devices 709 and 711, disk drives 715 and optional monitor 705. Fixed media 717, or fixed media 722 over port 719, may be used to program such a system and may represent a disk-type optical or magnetic media, magnetic tape, solid state dynamic or static memory, etc. In specific embodiments, the invention may be embodied in whole or in part as software recorded on this fixed media. Communication port 719 may also be used to initially receive instructions that are used to program such a system and may represent any type of communication connection.

Various programming methods and algorithms, including genetic algorithms and neural networks, can be used to perform aspects of the data collection, correlation, and storage functions, as well as other desirable functions, as described herein. In addition, digital or analog systems such as digital or analog computer systems can control a variety of other functions such as the display and/or control of input and output files. Software for performing the electrical analysis methods of the invention are also included in the computer systems of the invention.

Optionally, the integrated systems of the invention include an automated workstation. For example, such a workstation can prepare and analyze samples by performing a sequence of events including: preparing samples from a tissue or blood sample; exposing the samples to at least one patch clamp device comprising all or part of a library of candidate probe molecules; and detecting cell reactions by various electrical measurements. The cell reaction data is digitized and recorded in the appropriate database.

Automated and/or semi-automated methods for solid and liquid phase high-throughput sample preparation and evaluation are available, and supported by commercially available devices. For example, robotic devices for preparation of cells. Alternatively, or in addition, robotic systems for liquid handling are available from a variety of sources, e.g., automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Beckman Coulter, Inc. (Fullerton, Calif.)) which mimic the manual operations performed by a scientist. Any of the above devices are suitable for use with the present invention, e.g., for high-throughput analysis of library components or subject samples. The nature and implementation of modifications to these devices (if any) so that they can operate as discussed herein will be apparent to persons skilled in the relevant art.

Other Embodiments

Although the present invention has been described in terms of various specific embodiments, it is not intended that the invention be limited to these embodiments. Modification within the spirit of the invention will be apparent to those skilled in the art.

All publications, patents, and patent applications cited herein or filed with this submission, including any references filed as part of an Information Disclosure Statement, are incorporated by reference in their entirety.

What is claimed:

1. A multiple cell trapping device comprising:
 a substrate comprising:
  a planar surface;
  a main channel defined in part by the planar surface, the main channel having a length dimension and a width dimension, wherein the length dimension of said main channel is in a plane roughly parallel to the plane of the planar surface of said substrate;
  a plurality of lateral openings in a side of said main channel, wherein the plurality of lateral openings are defined in part by the planar surface;
  wherein at least two lateral openings from said plurality of lateral openings are each operatively connected to respective lateral trapping channels, wherein the respective lateral trapping channels are defined in part by the planar surface, and wherein the lateral trapping channels intersect the main channel at respective ones of the at least two lateral openings;
 a microfluidic input for introducing cells in a fluid to said main channel; and
 one or more microfluidic trapping connections for applying negative pressure to said at least two lateral openings such that cells in said main channel can be immobilized at said at last two lateral openings, wherein said cells are immobilized at said at least two lateral openings solely by the pressure difference between the pressure in said main channel and said negative pressure applied by said one or more connections; and
 one or more electrical connections for applying an electric field to a cell at one of said plurality of lateral openings.

2. The device according to claim 1 wherein:
 said substrate comprises an elastomer, and wherein said elastomer defines in part said main channel, said plurality of lateral openings, and the corresponding lateral trapping channels;
 said plurality of lateral openings have a cross section less than about 3 microns by 3 microns; and the corresponding lateral trapping channels have cross sections less than about 3 microns by 3 microns.

3. The device of claim 2 wherein said elastomer comprises PDMS.

4. The device of claim 1 wherein said negative pressure is generated by pneumatic controls.

5. The device of claim 1 wherein the device is controlled by computer software.

6. The device of claim 1 wherein said main channel is a flow-through channel.

7. The device of claim 1 wherein the one or more electrical connections comprise Ag/AgCl electrodes.

8. The device of claim 1 wherein said plurality of lateral openings are electrically connected to operate as independent patch channels.

9. The device of claim 1 wherein the device can generate gigaohm seals at said plurality of lateral openings.

10. The device of claim 1 further comprising one or more injection channels operatively connected to said main channel.

11. The device of claim 10 wherein said main channel and said one or more injection channels are all in roughly the same horizontal plane.

12. The device of claim 10 wherein said device permits high throughput screening of compounds.

13. The device of claim 10 wherein said one or more injection channels comprise an array of injection channels.

14. The device of claim 10 wherein said one or more injection channels are used for reagent delivery.

15. The device of claim 14 wherein reagent delivery is controlled by input pressures.

16. The device of claim 15 wherein said input pressures can be timed so that only one injection channel delivers reagent at a time.

17. The device of claim 15 wherein said input pressures can be timed so that multiple injection channels deliver reagent simultaneously.

18. The device of claim 1 wherein said plurality of lateral openings are spaced less than 40 microns apart.

19. The device of claim 1 wherein at least one electrode is connected to each respective lateral trapping channel.

20. The device of claim 1 wherein said plurality of lateral openings are arrayed about less than 30 microns apart.

21. The device of claim 1 wherein the height of each of said respective lateral trapping channels is about 3.1 µm.

22. The device of claim 1 wherein one or more electrodes are in one or more lateral trapping channels.

23. The device of claim 1 wherein said one or more microfluidic trapping connections are defined in part by the planar surface.

24. The device of claim 1 wherein the substrate comprises a unitary material and wherein the main channel and the corresponding lateral trapping channels are both defined in part by the unitary material.

25. The device of claim 1 wherein the planar surface defines a bottom of the main channel, the plurality of lateral openings, and the corresponding lateral trapping channels.

26. The device of claim 1, wherein said one or more electrical connections are configured to apply the electric field sufficient to electroporate the cell at one of said plurality of lateral openings.

27. A device comprising:
a substrate comprising:
a planar surface;
means for holding multiple cells in fluid suspension in a main channel, wherein said main channel comprises a length dimension and a width dimension, said length dimension of said main channel being in a plane parallel to the plane of the planar surface of said substrate, and wherein said main channel is defined in part by the planar surface; and
lateral cell trapping means formed in said substrate and operatively connected to said means for holding multiple cells in fluid suspension, said lateral cell trapping means comprising at least one trapping channel having a length dimension and a width dimension, wherein said length dimension is in a plane parallel to the plane of the planar surface of said substrate, wherein said at least one trapping channel intersects said main channel, and wherein said at least one trapping channel is defined in part by the planar surface;
means for applying negative pressure to said lateral cell trapping means in order to immobilize cells at said lateral cell trapping means, wherein said cells are immobilized at said lateral cell trapping means solely by the pressure difference between the pressure in said main channel and said negative pressure; and
means for applying an electric field between said means for holding multiple cells and said lateral trapping means.

28. The device according to claim 27 further comprising:
means for measuring electrical properties between said means for holding multiple cells and said lateral cell trapping means.

29. The device of claim 27 wherein the substrate comprises a unitary material and wherein the main channel and the at least one trapping channel are both defined in part by the unitary material.

30. The device of claim 27 wherein the planar surface defines a bottom of the main channel and the at least one trapping channel.

31. The device of claim 27 wherein said lateral cell trapping means comprises a plurality of trapping channels, wherein the plurality of trapping channels intersect the main channel at a plurality of lateral openings, and wherein the plurality of lateral openings are spaced less than 40 microns apart.

32. The device of claim 27 wherein said lateral cell trapping means comprises a plurality of trapping channels, wherein the plurality of trapping channels intersect the main channel at a plurality of lateral openings, and wherein the plurality of lateral openings are arrayed about less than 30 microns apart.

33. The device of claim 27, wherein said means for applying an electric field between said means for holding multiple cells and said lateral trapping means comprises means for applying the electric field sufficient to electroporate a cell immobilized at said lateral cell trapping means.

* * * * *